United States Patent
Gately et al.

(10) Patent No.: US 9,447,050 B2
(45) Date of Patent: Sep. 20, 2016

(54) SOLID FORMS OF CURCUMIN

(75) Inventors: Stephen T. Gately, Scottsdale, AZ (US); Steven J. Triezenberg, Ada, MI (US); Tong Wang, Phoenix, AZ (US)

(73) Assignees: THE TRANSLATIONAL GENOMICS RESEARCH INSTITUTE, Phoenix, AZ (US); VAN ANDEL RESEARCH INSTITUTE, Grand Rapids, MI (US)

( * ) Notice: Subject to any disclaimer, the term of this patent is extended or adjusted under 35 U.S.C. 154(b) by 234 days.

(21) Appl. No.: 14/009,589

(22) PCT Filed: Apr. 5, 2012

(86) PCT No.: PCT/US2012/032396
§ 371 (c)(1),
(2), (4) Date: Oct. 3, 2013

(87) PCT Pub. No.: WO2012/138907
PCT Pub. Date: Oct. 11, 2012

(65) Prior Publication Data
US 2014/0031403 A1   Jan. 30, 2014

Related U.S. Application Data

(60) Provisional application No. 61/471,802, filed on Apr. 5, 2011, provisional application No. 61/561,667, filed on Nov. 18, 2011.

(51) Int. Cl.
| | |
|---|---|
| C07D 235/26 | (2006.01) |
| C07C 49/248 | (2006.01) |
| C07C 229/26 | (2006.01) |
| C07D 235/30 | (2006.01) |
| A61K 31/12 | (2006.01) |
| A61K 31/4184 | (2006.01) |

(52) U.S. Cl.
CPC ............ *C07D 235/26* (2013.01); *A61K 31/12* (2013.01); *A61K 31/4184* (2013.01); *C07C 49/248* (2013.01); *C07C 229/26* (2013.01); *C07D 235/30* (2013.01)

(58) Field of Classification Search
None
See application file for complete search history.

(56) References Cited

U.S. PATENT DOCUMENTS

| | | |
|---|---|---|
| 2001/0003744 A1 | 6/2001 | Chamberlin |
| 2007/0060644 A1 | 3/2007 | Vander Jagt |
| 2010/0093667 A1 | 4/2010 | Graetz |
| 2010/0175141 A1 | 7/2010 | Collins |

FOREIGN PATENT DOCUMENTS

WO   WO2008/045534   4/2008

OTHER PUBLICATIONS

International Search Report, Written Opinion, and Search Strategy for International Application No. PCT/US12/32396 dated Sep. 21, 2012.
Sekhon BS, "Pharmaceutical co-crystals—a review" ARS Pharmaceutica [online], 2009 vol. 50, No. 2, pp. 99-117.
Nawrocka W. et al., "Synthesis and antiproliferative activity in vitro of 2-aminobenzimidazole derivatives"Il Farmaco [online] Feb. 2004, vol. 59, Iss. 2, pp. 83-91.
S. B. Kutluay et al. Curcumin inhibits Herpes Simplex Virus Immediate-early gene expression by a mechanism independent , Virology 2008 239-247 vol. 373.
K. Z. Bourne et al. Plant products as topical microbicide candidates . . . Antiviral Research 1999 219-226 vol. 42.

*Primary Examiner* — Rebecca Anderson
*Assistant Examiner* — Po-Chih Chen

(57) ABSTRACT

The present invention provides forms of curcumin and the pharmaceutical compositions thereof. The forms of curcumin disclosed herein are curcumin polymorph Form III, curcumin-2-aminobenzimidazole co-crystal, and curcumin-L-lysine co-crystal. Further, the invention provides methods inhibiting cancer cells and HSV-1 using these curcumin novel solid forms.

18 Claims, 48 Drawing Sheets

SOLID FORMS OF CURCUMIN

CROSS REFERENCE

This application is the national stage of International Patent Application No. PCT/US2012/032396, filed on Apr. 5, 2012, which claims the priority benefit of U.S. provisional application 61/471,802, filed on Apr. 5, 2011; U.S. provisional application 61/561,667, filed Nov. 18, 2011, the teachings and content of which are incorporated by reference herein.

FIELD OF THE INVENTION

The present invention generally relates to novel solid forms of curcumin, including curcumin polymorph and curcumin co-crystal forms, and more specifically to curcumin polymorph Form III, curcumin-2-aminobenzimidazole co-crystal, and curcumin-L-lysine co-crystal. Further, the invention provides methods inhibiting cancer cells and HSV-1 using these curcumin novel solid forms.

BACKGROUND OF THE INVENTION

Solid forms, including polymorphs and co-crystals, exist in either amorphous or crystalline forms. In the case of crystalline forms, molecules are positioned in three-dimensional lattice sites. When a compound recrystallizes from a solution or slurry, it may crystallize with different spatial lattice arrangements, and the different crystalline forms are sometimes referred to as "polymorphs." Further, a pharmaceutical co-crystal is a single crystalline solid that incorporates two neutral molecules, one being an API (Active Pharmaceutical Ingredient) and the other a co-crystal former. Co-crystallization alters the molecular interactions and composition of pharmaceutical materials. The different polymorph or co-crystal forms of a given API may differ from each other with respect to one or more chemical properties (e.g., dissolution rate, solubility), biological properties (e.g., bioavailability, pharmacokinetics), and/or physical properties (e.g., mechanical strength, compaction behavior, flow properties, particle size, shape, melting point, degree of hydration or salvation, caking tendency, compatibility with excipients).

Curcumin is a major constituent found in the spice tumeric, which is a dried powder from the rhizomes of *Curcuma longa* L. Several in vitro and in vivo studies demonstrated its suppression, retardation, or inversion of carcinogenesis. Some research also suggests that curcumin may help prevent or treat cancer. Furthermore, it also exhibits anti-inflammatory, antioxidant, antiviral, and anti-infectious activities and wound healing properties. Inhibition of arachidonic acid metabolism by curcumin has been suggested to be a key mechanism for its anticarcinogenic action. In addition, curcumin was found to inhibit herpes simplex virus 1 and 2 by controlling the immediate-early gene expression. However, curcumin has extremely poor water solubility and bioavailability. Because poor dissolution rate, solubility, chemical stability and moisture uptake influence therapeutic efficacy of many pharmaceuticals, and may therefore significantly lower the market value of a drug, there is a need to design new solid forms of curcumin for pharmaceutical use, such as polymorph or co-crystal forms of curcumin.

SUMMARY OF THE INVENTION

One aspect of the present invention provides a co-crystal form of curcumin, the co-crystal form being curcumin-2-aminobenzimidazole. The said co-crystal form, curcumin-2-aminobenzimidazole, exhibits an X-ray powder diffraction pattern having characteristic peaks expressed in degrees 2-theta at about 6.2, about 9.0, about 12.3, about 14.5, about 17.3, about 18.0, about 19.0, about 20.0, about 21.2, about 24.5, about 25.05, and about 27.1. In particular, the co-crystal form, curcumin-2-aminobenzimidazole, exhibits an endothermic transition with an onset of about 118.1° C. as measured by differential scanning calorimetry.

Another aspect of the invention provides a pharmaceutical composition comprising curcumin-2-aminobenzimidazole and at least one pharmaceutically acceptable excipient. Specifically, curcumin-2-aminobenzimidazole exhibits an X-ray powder diffraction pattern having characteristic peaks expressed in degrees 2-theta at about 6.2, about 9.0, about 12.3, about 14.5, about 17.3, about 18.0, about 19.0, about 20.0, about 21.2, about 24.5, about 25.05, and about 27.1 and an endothermic transition with an onset of about 118.1° C. as measured by differential scanning calorimetry. In addition, curcumin-2-aminobenzimidazole exhibits improved anticarcinogenic effect in comparison to curcumin. For this particular pharmaceutical composition, curcumin-2-aminobenzimidazole inhibits HSV-1 (Herpes simplex virus 1) through suppressing ICP0 gene expression.

Yet another aspect of the present invention provides a co-crystal form of curcumin, curcumin-L-lysine. Curcumin-L-lysine is an amorphous form of curcumin co-crystal that exhibits a first exotherm at onset 36.7° C. with peak 43.6° C.; a second exotherm at onset 93.7° C. with peak 97.8° C.; and an endotherm at onset 135.5° C. with peak 136.0° C.

Still another aspect of the present invention provides a pharmaceutical composition comprising curcumin-L-lysine and at least one pharmaceutically acceptable excipient. Specifically, the curcumin-L-lysine in the composition exhibits a first exotherm at onset 36.7° C. with peak 43.6° C.; a second exotherm at onset 93.7° C. with peak 97.8° C.; and an endotherm at onset 135.5° C. with peak 136.0° C. In addition, curcumin-L-lysine in the composition exhibits improved anticarcinogenic effect in comparison to curcumin. Also, curcumin-L-lysine inhibits HSV-1 (Herpes simplex virus 1) through suppressing ICP0 gene expression.

Yet still another aspect of the present invention provides a polymorph form of curcumin, the polymorph form being Form III. Specifically, Form III exhibits an X-ray powder diffraction pattern having characteristic peaks expressed in degrees 2-theta at about 9.56, about 14.51, about 17.90, and about 26.86. Form III also exhibits an endothermic transition with an onset of about 162.6° C. as measured by differential scanning calorimetry.

Another aspect of the present invention provides a pharmaceutical composition comprising polymorph Form III of curcumin, and at least one pharmaceutically acceptable excipient. Specifically, the polymorph Form III exhibits an X-ray powder diffraction pattern having characteristic peaks expressed in degrees 2-theta at about 9.56, about 14.51, about 17.90, and about 26.86 and an endothermic transition with an onset of about 162.6° C. as measured by differential scanning calorimetry. The polymorph Form III in this pharmaceutical composition exhibits improved anticarcinogenic effect in comparison to curcumin. In addition, the pharmaceutical composition of claim 18, wherein polymorph Form III inhibits HSV-1 (Herpes simplex virus 1) through suppressing ICP0 gene expression.

An additional aspect of the present invention provides a pharmaceutical composition comprising at least one polymorph or an amorphous form of curcumin or a curcumin co-crystal selected from the group consisting of curcumin polymorph Form III, curcumin-2-aminobenzimidazole and curcumin-L-lysine and at least one pharmaceutically acceptable excipient. Specifically, the curcumin polymorph Form III in the pharmaceutical composition exhibits an X-ray powder diffraction pattern having characteristic peaks expressed in degrees 2-theta at about 9.56, about 14.51, about 17.90, and about 26.86 and an endothermic transition with an onset of about 162.6° C. as measured by differential scanning calorimetry. Alternatively, the curcumin co-crystal of the pharmaceutical composition is selected from the group consist of curcumin-2-aminobenzimidazole and curcumin-L-lysine. Specifically, the curcumin-2-aminobenzimidazole co-crystal exhibits an X-ray powder diffraction pattern having characteristic peaks expressed in degrees 2-theta at about 6.2, about 9.0, about 12.3, about 14.5, about 17.3, about 18.0, about 19.0, about 20.0, about 21.2, about 24.5, about 25.05, and about 27.1 and an endothermic transition with an onset of about 118.1° C. as measured by differential scanning calorimetry. Whereas, the curcumin-L-lysine exhibits a first exotherm at onset 36.7° C. with peak 43.6° C.; a second exotherm at onset 93.7° C. with peak 97.8° C.; and an endotherm at onset 135.5° C. with peak 136.0° C.

A further aspect of the present invention provides a method of inhibiting cancer cell growth, and the method comprises administering an effective dosage amount of a polymorph, an amorphous form or a co-crystal form of curcumin selected from the group consisting of curcumin polymorph Form III, curcumin-2-aminobenzimidazole and curcumin-L-lysine.

Still another aspect of the present invention provides a method of inhibiting the growth of HSV-1, and the method comprises administering an effective dosage amount of a polymorph, an amorphous form or a co-crystal form of curcumin selected from the group consisting of curcumin polymorph Form III, curcumin-2-aminobenzimidazole and curcumin-L-lysine.

Other aspects and iterations of the invention are described in more detail below.

DETAILED DESCRIPTION OF THE INVENTION

Figure 1:
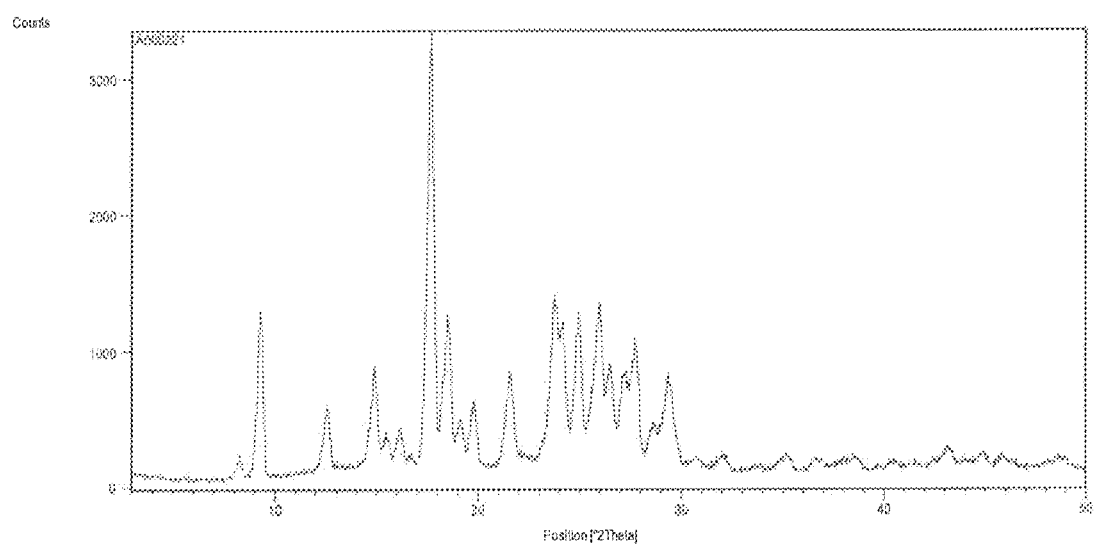
FIG. 1 depicts an X-ray powder diffraction (XRPD) pattern of input material of curcumin crystalline. Peak intensity is plotted as a function of degrees 2-theta.

Six polymorphs of curcumin were observed in the polymorph screen, among which two forms are developable. Form I, known in the art, is the form of the input material, and it is the predominate polymorph observed in the screen. Form III is a novel polymorph in anhydrous form that is non-hygroscopic. Form III is a meta-stable form that transforms at low temperature. Form II and Form V are 1,4-dioxane solvate, Form IV is unknown, and Form VI is a methyl acetate solvate.

Further the co-crystal screen with co-formers was carried out on Form III. Eight co-crystals were located, among which three were fully analyzed: curcumin-2-aminobenzimidazole, curcumin-nicotinamide and curcumin-L-lysine. Curcumin-2-aminobenzimidazole and curcumin-nicotinamide were scaled-up and further assessed.

The present invention thus provides one novel form of curcumin polymorph Form III. The invention also provides two novel curcumin co-crystals: curcumin-2-aminobenzimidazole and curcumin-L-lysine, both of which exhibited improved physiochemical properties. The present invention further provides a pharmaceutical composition comprising co-crystal curcumin-2-aminobenzimidazole, curcumin-L-lysine or polymorph Form III.

(I) Polymorph and Co-Crystal Forms of Curcumin (a) Curcumin Polymorph

Polymorphs have different stabilities and may spontaneously convert from a metastable form (unstable form) to the stable form at a particular temperature. In addition, they exhibit different melting points and solubilities which affect the dissolution rate of drug, and thereby, its bioavailability in the body.

A first aspect of the invention encompasses two crystalline forms of curcumin polymorphs. The two polymorphs may be distinguished on the basis of different X-ray powder diffraction patterns. Form I is stable over a wide range of temperature and relative humidity conditions. Form III transforms at temperatures as low as 40° C. The two crystalline forms also may be distinguished on the basis of different endothermic transitions or melting temperatures, as determined by differential scanning calorimetry (DSC). Those of skill in the art will appreciate that other analytical techniques, such as X-ray powder diffraction analysis (XRPD), nuclear magnetic resonance (NMR), high performance liquid chromatography-ultraviolet detection (HPLC-UV), thermogravimetric/differential thermal analysis (TG/DTA), dynamic vapor sorption (DVS), polarized light microscopy (PLM), etc., also may be used to distinguish these crystalline forms.

Crystalline curcumin may exist as Form I. Crystalline Form I curcumin exhibits an X-ray powder diffraction pattern comprising characteristic peaks expressed in degrees 2-theta. In particular, Form I exhibits predominant peaks expressed in degrees 2-theta at about 9.63, about 18.12, about 24.12, 26.34, 27.58, and about 19.64. Form I also exhibits significant peaks at about 8.87, about 13.08, about 15.28, about 18.98, about 19.62, about 22.06, about 25.40, and about 29.64 in degrees 2-theta.

Crystalline curcumin may also exist as polymorph Form III. Crystalline Form III curcumin exhibits an X-ray powder diffraction pattern comprising characteristic peaks expressed in degrees 2-theta. In particular, Form III exhibits predominant peaks expressed in degrees 2-theta at about 9.56, about 14.51, about 17.90, and about 26.86. Form I also exhibits significant peaks at about 8.56, about 15.12, about 15.56, about 16.60, about 18.76, about 19.37, about 20.05, about 21.88, about 27.31, about 27.99 and about 28.74 in degrees 2-theta.

Curcumin crystals may exist as polymorph Form II, which is a 1,4-dioxane solvate. Curcumin crystals may also exist as polymorph Form V, which is a 1,4-dioxane solvate. Alternatively, curcumin crystals may exist as polymorph Form VI, which is a methyl acetate solvate.

(b) Curcumin Co-Crystal

Pharmaceutical co-crystal comprises API and a stoichiometric amount of a pharmaceutically acceptable co-crystal former. Pharmaceutically acceptable co-crystal former does not affect pharmacological activity of API but can improve its physical properties, such as solubility, hygroscopicity, compaction behavior, stability and bioavailability.

Various types of studies on co-crystals involve i) selection of co-crystal formers for a specific API, ii) co-crystal screening of pharmaceutical active ingredients with selected co-crystal formers, iii) development of reliable procedures to prepare pharmaceutical co-crystals, iv) characterization of pharmaceutical co-crystals, v) scale up of pharmaceutical co-crystals, and vi) co-crystal polymorphism.

The ability of an API to form a co-crystal is dependent on a range of variables. Experimental screening for co-crystal formers is not trivial. Synthesis and processing of co-crystals can be accomplished via a number of methods, including, for example, slow solvent evaporation crystallization from solution, solvent-reduced (e.g., slurrying, solvent-drop grinding) and solvent-free (e.g., grinding, melt), high throughput crystallization and co-sublimation techniques. Co-crystal high throughput screening provides information on relationship between formation and chemical structure of the API and co-formers. Factors affecting co-crystal stability include, for example, the types of co-former, the API/co-former ratio, the solvents, the temperature, the pressure, and the crystallization technique. A co-crystal is only expected to form if it is thermodynamically more stable than the crystals of its components. Phase transformations induced during processing/storage affect the mechanisms of conversion of crystalline drugs to co-crystals. Co-crystals can be constructed through several types of interaction, including hydrogen bonding, pi-stacking, and van der Waals forces.

Co-crystal former may be an excipient or another drug. Pharmaceutical co-crystal technology is used to identify and develop new forms of widely prescribed drugs and offer a chance to increase the number of forms of an API. In one embodiment, a pharmaceutically acceptable co-crystal former is selected from isonicotinamide, 4-aminopyridine, hydantoin, L-histidine, nicotinamide, L-lysine, allantoin, L-cysteine, L-tyrosine, meglumine, succinamide, urea, L-alanine, L-arginine, L-glutamine, L-tryptophan, L-serine, L-proline, L-asparagine, Salicylhydroxamic acid, Saccharin, Salicylaldoxime, 3-Aminobenzoic acid, 2-Aminobenzimidazole, and other co-crystal formers known in the art.

Co-crystals with the same active pharmaceutical ingredient (API) will have strikingly different pharmaceutical properties (melting point, solubility, dissolution, bioavailability, moisture uptake, chemical stability, etc.), depending on the nature of the second component. Some of the co-crystals formed had higher and some lower melting points as compared to their pure components. One aspect of the present invention provides curcumin polymorph Form III being an API for co-crystal construction and screening.

After co-crystal screening, the characterization of co-crystals involves both structure and physical properties. Non-limiting methods of structure property analysis include infrared spectroscopy, single crystal x-ray crystallography and powder x-ray diffraction. Non-limiting methods of physical property analysis include melting point apparatus, differential scanning calorimetry, and thermogravimetric analysis.

(i) curcumin-2-aminobenzimidazole

The co-crystallization may use 2-Aminobenzimidazole as a co-crystal former. The resulting form, curcumin-2-aminobenzimidazole, is an anhydrous co-crystal that is non-hygroscopic. The $^1$H NMR confirmed co-crystal formation was successful. The aromatic protons of the 2-aminobenzimidazole are accounted for by peaks at 7.1 ppm. The spectrum integrates to a 1:1 stoichiometry. Curcumin-2-aminobenzimidazole exhibits an X-ray powder diffraction pattern comprising characteristic peaks expressed in degrees 2-theta at about 6.2, about 9.0, about 12.3, about 14.5, about 17.3, about 18.0, about 19.0, about 20.0, about 21.2, about 24.5, about 25.05, and about 27.1. Curcumin-2-aminobenzimidazole also exhibits an endothermic transition with an onset of about 118.1° C. as measured by differential scanning calorimetry thermogram. Curcumin-2-aminobenzimidazole is stable under a range of conditions; temperature, humidity, ambient light and water, with no signs of degradation, disproportionation or loss of crystallinity.

(ii) curcumin-nicotinamide

The co-crystallization may use nicotinamide as a co-crystal former. The resulting form, curcumin-nicotinamide, is an anhydrous co-crystal that is moderately/highly hygroscopic. The preparation method is not fully robust as free API and co-former were still present. The stability of the material was good under a range of conditions: temperature, humidity and ambient light, with no signs of degradation or disproportionation, however when slurrying in water a loss of crystallinity was observed.

The $^1$H NMR confirmed co-crystal formation was successful. Curcumin-nicotinamide exhibits an X-ray powder diffraction pattern comprising characteristic peaks expressed in degrees 2-theta at about 9.0, about 12.2, about 15.0, about 17.5, about 18.5, about 23.5, about 24.5, about 25.4 and about 27.2. An endothermic transition with an onset of about 99.9° C. as measured by differential scanning calorimetry thermogram. XRPD indicated good crystalline. Analysis by XRPD post the DVS experiment confirmed no degradation or transformation had occurred.

All stability and slurrying in water experiments with curcumin-nicotinamide matched with primary material, showing no signs of form transformation, disproportionation, and degradation. However, a loss in crystallinity was observed as the time points increased of the slurrying in water experiment (FIG. 26b). The intrinsic dissolution rate of curcumin-nicotinamide is 0.040, approximately two times greater than that of the curcumin-2-aminobenzimidazole co-crystal and is, therefore, superior. The intrinsic dissolution rate is shown in Table 3.

(iii) curcumin-L-lysine

The co-crystallization may use L-lysine as a co-crystal former. The resulting form, curcumin-L-lysine remained amorphous during storage tests, slurrying in water and DVS analysis. Curcumin-L-lysine remained amorphous during storage tests, slurrying in water and DVS analysis. The material remained predominantly amorphous during thermodynamic solubility studies, although 2-3 small peaks could be seen by XRPD analysis. Curcumin-L-lysine exhibits a first exotherm at onset 36.7° C. with peak 43.6° C.; a second exotherm at onset 93.7° C. with peak 97.8° C.; and an endotherm at onset 135.5° C. with peak 136.0° C. The thermodynamic solubility of curcumin-L-lysine is very low. A dissolution rate of curcumin-L-lysine is 0.029.

(II) Biological Activities of Curcumin

Curcumin, a substance found in the spice turmeric, has long been used in Asian medicine to treat a variety of maladies. Now some research suggests that curcumin may help prevent or treat cancer. Curcumin is thought to have antioxidant properties, which means it may decrease swelling and inflammation. It's being explored as a cancer treatment in part because inflammation appears to play a role in cancer. Laboratory and animal research suggests that curcumin may prevent cancer, slow the spread of cancer, make chemotherapy more effective and protect healthy cells from damage by radiation therapy. Curcumin is being studied for use in many types of cancer.

Curcumin targets many causative factors involved in cancer development. By blocking the inflammatory master molecule nuclear factor-kappaB (or NF-kB), curcumin blunts cancer-causing inflammation, slashing levels of inflammatory cytokines throughout the body. Curcumin also interferes with production of dangerous advanced glycation end products that trigger inflammation which can lead to cancerous mutation. Curcumin alters cellular signaling to enhance healthy control over cellular replication, which tightly regulates the cellular reproductive cycle, helping to stop uncontrolled proliferation of new tissue in tumors. It promotes apoptosis in rapidly reproducing cancer cells without affecting healthy tissue and reins in tumor growth by making tumors more vulnerable to pharmacologic cell-killing treatments. In addition, curcumin regulates tumor suppressor pathways and triggers mitochondrial-mediated death in tumor tissue, thereby increasing the death of cancer cells. Finally, curcumin interferes with tumor invasiveness and blocks molecules that would otherwise open pathways to penetration of tissue. It also helps to starve tumors of their vital blood supply and it can oppose many of the processes that permit metastases to spread. These multi-targeted actions are central to curcumin's capacity to block multiple forms of cancer before they manifest. The multi-targeted mechanisms of curcumin have yielded compelling results in combating a remarkably broad array of cancers, including those of the breast, uterus, cervix, prostate, and GI tract. A burgeoning body of research demonstrates curcumin's potential to counter cancers of the blood, brain, lung, and bladder as well.

Curcumin is known to have antiviral effects as well. For example, it inhibits the expression of ICP0 in a dose-dependent manner. ICP0 is an immediate-early (IE) regulatory protein, and is a potent activator of herpes simplex virus type 1 gene expression in lytic infection and in the establishment and reactivation of latency in vivo.

Drugs in pharmaceutical compositions can be prepared in a variety of different forms. Such drugs can be prepared so as to have a variety of different chemical forms including chemical derivatives or salts. Such drugs can also be prepared to have different physical forms. For example, the drugs may be amorphous or may have different crystalline polymorphs, perhaps existing in different solvation or hydration states. By varying the form of a drug, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapor pressure, density, color, and compressibility.

The efficacy of different polymorph or co-crystal forms of curcumin may be tested using methods known in the art, including the method determining whether a compound reduces the number of cancer cells, whether a compound induces apoptosis, whether a compound decreases tumor metastasis. An IC50 value may be determined and used for comparative purposes in these tests. This value is the concentration of drug needed to inhibit tumor cell growth or induce cell death by 50% relative to the control. In addition, dose response analyses may be carried out to evaluate the potency of curcumin polymorph, amorphous form or co-crystal form to inhibit the growth of cancer cells or viruses.

(III) Pharmaceutical Compositions

Another aspect of the invention provides for pharmaceutical compositions comprising co-crystal form of curcumin. In general, the pharmaceutical composition will comprise an effective dosage amount of co-crystal form of curcumin, i.e., an amount of curcumin co-crystal sufficient to provide treatment to the subject being administered the pharmaceutical composition. Determination of an effective amount of the compound is within the capability of those skilled in the art, especially in light of the detailed disclosure provided herein. The effective amount of a pharmaceutical composition used to affect a particular purpose, as well as its toxicity, excretion, and overall tolerance may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the pharmaceutical composition in experimental animals. The exact techniques used in determining an effective amount will depend on factors such as the type, physical and/or chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of compound for addition to a cancer cell also includes the determination of an effective therapeutic amount, including the formulation of an effective dose range for use in vivo, including in humans.

In some embodiments, the pharmaceutical composition may comprise substantially pure curcumin co-crystal, as defined above. In one embodiment, the curcumin co-crystal is curcumin-2-aminobenzimidazole. In another embodiment, the curcumin co-crystal is curcumin-L-lysine. In other embodiments, the pharmaceutical composition may further comprise another crystalline or amorphous form of curcumin. For example, the pharmaceutical composition may further comprise curcumin-L-lysine in addition to curcumin-2-aminobenzimidazole. The amount of curcumin-L-lysine in such pharmaceutical compositions, therefore, may range from about 97%, about 95%, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, or about 3% by weight of the total amount of the curcumin solid forms.

A variety of excipients commonly used in pharmaceutical formulations may be selected on the basis of several criteria, such as, the desired dosage form and the release profile properties of the dosage form. Non-limiting examples of suitable excipients include an agent selected from the group consisting of a binder, a filler, a non-effervescent disintegrant, an effervescent disintegrant, a preservative, a diluent, a flavoring agent, a sweetener, a lubricant, an oral dispersing agent, a coloring agent, a taste masking agent, a pH modifier, a stabilizer, a compaction agent, and combinations of any of these agents.

In one embodiment, the excipient may be a binder. Suitable examples of binders include starches, pregelatinized starches, gelatin, polyvinylpyrolidone, cellulose, methylcellulose, sodium carboxymethylcellulose, ethylcellulose, polyacrylamides, polyvinyloxoazolidone, polyvinylalcohols, C12-C18 fatty acid alcohol, polyethylene glycol, polyols, saccharides, oligosaccharides, polypeptides, peptides, and combinations thereof.

In another embodiment, the excipient may be a filler. Suitable fillers include carbohydrates, inorganic compounds, and polyvinilpirrolydone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, and sorbitol.

The excipient may be a non-effervescent disintegrant. Suitable examples of non-effervescent disintegrants include starches (such as corn starch, potato starch, and the like), pregelatinized and modified starches thereof, sweeteners, clays (such as bentonite), micro-crystalline cellulose, alginates, sodium starch glycolate, and gums (such as agar, guar, locust bean, karaya, pecitin, and tragacanth).

In another embodiment, the excipient may be an effervescent disintegrant. By way of non-limiting example, suitable effervescent disintegrants include sodium bicarbonate in combination with citric acid, and sodium bicarbonate in combination with tartaric acid.

The excipient may comprise a preservative. Suitable examples of preservatives include antioxidants (such as alpha-tocopherol or ascorbate) and antimicrobials (such as parabens, chlorobutanol or phenol). In other embodiments, an antioxidant such as butylated hydroxytoluene (BHT) or butylated hydroxyanisole (BHA) may be utilized.

In another embodiment, the excipient may include a diluent. Examples of diluents suitable for use include pharmaceutically acceptable saccharides such as sucrose, dextrose, lactose, microcrystalline cellulose, fructose, xylitol, and sorbitol; polyhydric alcohols; starches; pre-manufactured direct compression diluents; and mixtures of any of the foregoing.

The excipient may include flavoring agents. Flavoring agents may be chosen from synthetic flavor oils and flavoring aromatics and/or natural oils, extracts from plants, leaves, flowers, fruits, and combinations thereof. By way of example, these may include cinnamon oils, oil of wintergreen, peppermint oils, clover oil, hay oil, anise oil, eucalyptus, vanilla, citrus oils (such as lemon oil, orange oil, grape and grapefruit oil), and fruit essences (such as apple, peach, pear, strawberry, raspberry, cherry, plum, pineapple, and apricot).

In another embodiment, the excipient may include a sweetener. By way of non-limiting example, the sweetener may be selected from glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; stevia-derived sweeteners; chloro derivatives of sucrose such as sucralose; sugar alcohols such as sorbitol, mannitol, sylitol, and the like. Also contemplated are hydrogenated starch hydrolysates and the synthetic sweetener 3,6-dihydro-6-methyl-1,2,3-oxathiazin-4-one-2,2-dioxide, particularly the potassium salt (acesulfame-K), and sodium and calcium salts thereof.

In another embodiment, the excipient may be a lubricant. Suitable non-limiting examples of lubricants include magnesium stearate, calcium stearate, zinc stearate, hydrogenated vegetable oils, sterotex, polyoxyethylene monostearate, talc, polyethyleneglycol, sodium benzoate, sodium lauryl sulfate, magnesium lauryl sulfate, and light mineral oil.

The excipient may be a dispersion enhancer. Examples of suitable dispersants include starch, alginic acid, polyvinylpyrrolidones, guar gum, kaolin, bentonite, purified wood cellulose, sodium starch glycolate, isoamorphous silicate, and microcrystalline cellulose.

Depending upon the embodiment, it may be desirable to provide a coloring agent. Suitable color additives include food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in the present invention depending on the embodiment.

The excipient may include a taste-masking agent. Examples of taste-masking materials include cellulose hydroxypropyl ethers (HPC); low-substituted hydroxypropyl ethers (L-HPC); cellulose hydroxypropyl methyl ethers (HPMC); methylcellulose polymers and mixtures thereof; polyvinyl alcohol (PVA); hydroxyethylcelluloses; carboxymethylcelluloses and salts thereof; polyvinyl alcohol and polyethylene glycol co-polymers; monoglycerides or triglycerides; polyethylene glycols; acrylic polymers; mixtures of acrylic polymers with cellulose ethers; cellulose acetate phthalate; and, combinations thereof.

In various embodiments, the excipient may include a pH modifier. In certain embodiments, the pH modifier may include sodium carbonate or sodium bicarbonate.

The weight fraction of the excipient or combination of excipients in the pharmaceutical composition may be about 98% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the pharmaceutical composition.

The pharmaceutical compositions detailed herein may be manufactured in one or several dosage forms. Suitable dosage forms include transdermal systems or patches. The transdermal system may be a matrix system, a reservoir system, or a system without rate-controlling membranes. Other suitable dosage forms also include tablets, including suspension tablets, chewable tablets, effervescent tablets or caplets; pills; powders such as a sterile packaged powder, a dispensable powder, and an effervescent powder; capsules including both soft or hard gelatin capsules such as HPMC capsules; lozenges; a sachet; a sprinkle; a reconstitutable powder or shake; a troche; pellets such as sublingual or buccal pellets; granules; liquids for oral or parenteral administration; suspensions; emulsions; semisolids; or gels.

The dosage forms may be manufactured using conventional pharmacological techniques. Conventional pharmacological techniques include, e.g., one or a combination of methods: (1) dry mixing, (2) direct compression, (3) milling, (4) dry or non-aqueous granulation, (5) wet granulation, or (6) fusion. See, e.g., Lachman et al., The Theory and Practice of Industrial Pharmacy (1986). Other methods include, e.g., prilling, spray drying, pan coating, melt granulation, granulation, wurster coating, tangential coating, top spraying, extruding, coacervation and the like.

Among other uses, in general, the pharmaceutical compositions of the invention will be used in operating rooms, intensive care units, or palliative care units. The pharmaceutical compositions, and in particular transdermal delivery systems, may also be used for the management of other clinical conditions.

The amount of active ingredient that is administered to a subject can and will vary depending upon a variety of factors such as the age and overall health of the subject, and the particular mode of administration. Those skilled in the art will appreciate that dosages may also be determined with guidance from Goodman & Goldman's The Pharmacological Basis of Therapeutics, Tenth Edition (2001), Appendix II, pp. 475-493, and the Physicians' Desk Reference.

EXAMPLES

The following examples illustrate the invention.

Materials and Methods for Examples

Material:

The starting curcumin material is an orange crystalline powder that weighs 50 g (Batch/Lot/Sample ID: A0271904; SFS ID: A000221)

Nuclear Magnetic Resonance (NMR):

NMR experiments were performed on a Bruker 400 MHz. 1H experiments of each sample were performed in d-DMSO and each sample was prepared to ca. 10 mg concentration.

High Performance Liquid Chromatography-Ultraviolet Detection (HPLC-UV):

Instrument used was the Agilent 1200 model, the column was Waters XBridge C18 5 Fm (4.6×250 mm), with temperature at 33° C. The Mobile Phase was acetonitrile: 2% acetic acid (40:60, v/v). Other parameters were as follows—Elution: Isocratic (run time: 20 mins); λ: 425 nm; Injection Volume: 40 FI; Flow Rate: 1.4 ml/min.

X-Ray Powder Diffraction (XRPD):

XRPD analysis was carried out on a Siemens D5000, scanning the samples between 3 and 30 or 50 °2θ. For samples <100 mg, about 5 mg of sample was gently compressed onto a glass slide which fitted into the sample holder. For samples >100 mg; ca. 100 mg of sample was gently compressed into a plastic sample holder, so that the sample surface was smooth and just above the level of the sample holder. The sample was then loaded into the diffractometer running in reflection mode and analyzed, using the following experimental conditions—Raw Data Origin: Siemens-binary V2 (.RAW); Start Position [°2Th.]: 3.0000; End Position [°2Th.]: 30.000 or 50.000; Step Size [°2Th.]: 0.0200; Scan Step Time: [s] 0.8; Scan Type: Continuous; Offset [°2Th.]: 0.0000; Divergence Slit Type: Fixed; Divergence Slit Size [°]: 2.0000; Specimen Length [mm]: various; Receiving Slit Size [mm]: 0.2000; Measurement Temperature [° C.]: 20.00; Anode Material: Cu; K-Alpha1 [A]: 1.54060; K-Alpha2 [A]: 1.54443; K-Beta [A]: 1.39225; K-A2/K-A1 Ratio: 0.50000 (nominal); Generator Settings 40 mA, 40 kV; Diffractometer Type: D5000; Diffractometer Number: 0; Goniometer Radius [mm]: 217.50; Incident Beam Monochromator: No; Diffracted Beam Monochromator: Graphite; Spinning: No.

Differential Scanning calorimetry (DSC):

Approximately, 5 mg of sample was weighed into an aluminum DSC pan and sealed with a pierced aluminum lid (non-hermetically). The sample pan was then loaded into a Seiko DSC 6200 (equipped with a cooler) cooled and held at 25° C. Once a stable heat-flow response was obtained, the sample and reference were then heated to ca. 230° C. at scan rate of 10° C./min and the resulting heat flow response monitored. Prior to analysis, the instrument was temperature and heat-flow calibrated using an indium reference standard. Sample analysis was carried out by Muse measurement software where the temperatures of thermal events were quoted as the onset temperature, measured according to the manufacturer's specifications.

Thermogravimetric/Differential Thermal Analysis (TG/DTA):

Approximately, 5 mg of sample was accurately weighed into an aluminum pan and loaded into a Seiko TG/DTA 6200 simultaneous thermogravimetric/differential thermal analyzer and held at room temperature. The sample was then heated at a rate of 10° C./min from 25° C. to 300° C. during which time the change in sample weight was monitored along with any thermal events (DTA). Nitrogen was used as the purge gas, at a flow rate of 20 cm$^3$/min. Prior to analysis the instrument was weight and temperature calibrated using a 100 mg reference weight and an indium reference standard, respectively.

Dynamic Vapor Sorption (DVS):

Approximately, 10 mg of sample was placed into a wire-mesh vapor sorption balance pan and loaded into a DVS-1 dynamic vapor sorption balance by Surface Measurement Systems. The sample was subjected to a ramping profile from 20-90% relative humidity (RH) at 10% increments, maintaining the sample at each step until a stable weight was achieved (99.5% step completion). After completion of the sorption cycle, the sample was then dried using the same procedure, but all the way down to 0% RH and finally taken back to the starting point of 20% RH. The weight change during the sorption/desorption cycles was then plotted, allowing for the hygroscopic nature of the sample to be determined.

Polarized Light Microscopy (PLM):

The presence of birefringence was determined using an Olympus BX50F4 polarizing microscope, equipped with a Motic camera and image capture software (Motic Images Plus 2.0). Images were recorded using 20× objective. Approximately 1 mg of sample was placed onto a microscope slide in each case.

Solvent Solubility Screen:

Approximately, 25 mg portions of the API were placed in 24 different vials. 5 volume aliquots of the appropriate solvent system were added to the correct vial. Between each addition, the mixture was checked for dissolution and if no dissolution was apparent, the mixture was warmed to 50° C., and checked again. The procedure was continued until dissolution was observed or when 100 volumes of solvent had been added.

Temperature Cycling Experiments:

Using the information gathered from the solubility approximations, slurries of the sample were prepared in the 24 selected solvent systems. The slurries were temperature cycled between RT and 40° C., in 4 hour cycles for a period of 72 hours. The solids were visually checked for any obvious signs of degradation (i.e., color changes) and then, if not degraded, isolated by filtration. The solids were allowed to dry at ambient conditions for about 24 hours prior to analysis.

Crash Cooling Experiments:

Crash cooling experiments were performed by placing saturated solutions of the sample, in the selected solvent systems, in environments of 4° C. and −21° C. for approximately 48 hours. Any solid material was recovered and the solids were allowed to dry at ambient conditions for about 24 hours prior to analysis.

Rapid Evaporation Experiments:

Rapid evaporation experiments were conducted by allowing saturated solutions of the sample to evaporate under nitrogen at ambient conditions. Once the material had evaporated to dryness it was then recovered and the solid material analyzed.

Anti-Solvent Addition Experiments:

Anti-solvent addition experiments were conducted by adding the anti-solvent, water, to saturated solutions of the sample, in the selected solvent systems. The addition was continued until there was no further precipitation observed. These experiments were carried out at various temperatures; ambient and 4° C. The solid was isolated and then dried at ambient conditions for about 24 hours prior to analysis.

Reverse Anti-Solvent Addition Experiments:

Saturated solutions of the samples, in the selected solvent systems, were added to the antisolvent, water. These experiments were carried out at various temperatures; ambient and 4° C. The solid was isolated and then dried at ambient conditions for about 24 hours prior to analysis.

Intrinsic Dissolution Experiments:

Approximately, 80-180 mg of each form was compressed into discs (or added as powders) by placing the material into a die (diameter: 13 mm) and compressing the die under 5 tons of pressure in a hydraulic press for about 2 minutes. The dissolution instrument, Sotax AT7 conformed to EP2 and USP2 in which paddles were used to stir the media. Each form was tested in 1% solutol solution (samples in 100% water had concentrations below the limit of detection of the system, therefore could not be quantified), in the stationary disc mode (i.e., discs were added at time=0 seconds and allowed to sink to the bottom of the media). Approximately 1 ml aliquots of media were extracted from the dissolution vessels at times 1, 5, 10, 15, 30, 60, 120, 240 minutes and 24 hours, and tested for API concentration by HPLC-UV. Dissolution curves were plotted and from the first 5 or 6 points on the curves the intrinsic dissolution rate curves were calculated. All tests were carried out at 37° C. and a paddle speed of 150 rpm.

Polymorph Stability Studies:

Competitive slurry experiments were carried out between each of the forms, in up to four solvent systems at RT and 60° C. ca. 50:50 mix (50 mg) of each form was placed into the appropriate solvent system, at the appropriate temperature, and shaken for ca. 48 hours. The resulting solid was analyzed by XRPD to determine the form.

Preparation of Curcumin-Nicotinamide Co-Crystal:

Approximately 300 mg of the API and 99.4 mg of nicotinamide were ground together with 3-4 drops of ethyl acetate for ca. 1 hour in the ball mill. After preparation the sample was analyzed by XRPD to asses if co-crystallization was complete.

Preparation of curcumin-2-aminobenzimidazole Co-Crystal:

Approximately 300 mg of API and 133 mg of 2-aminobenzimidazole were ground together with 3-4 drops of methyl isobutyl ketone for ca. 1 hour in the ball mill. After preparation the sample was analyzed by XRPD to assess if co-crystallization was complete.

Preparation of curcumin-L-lysine Co-Crystal:

Approximately 250 mg of API and 99.2 mg of L-lysine were dry ground together for ca. 1 hour in the ball mill. After preparation the sample was analyzed by XRPD to assess whether the material was amorphous.

Example 1

Characterization of Curcumin Input Material

Figure 2:
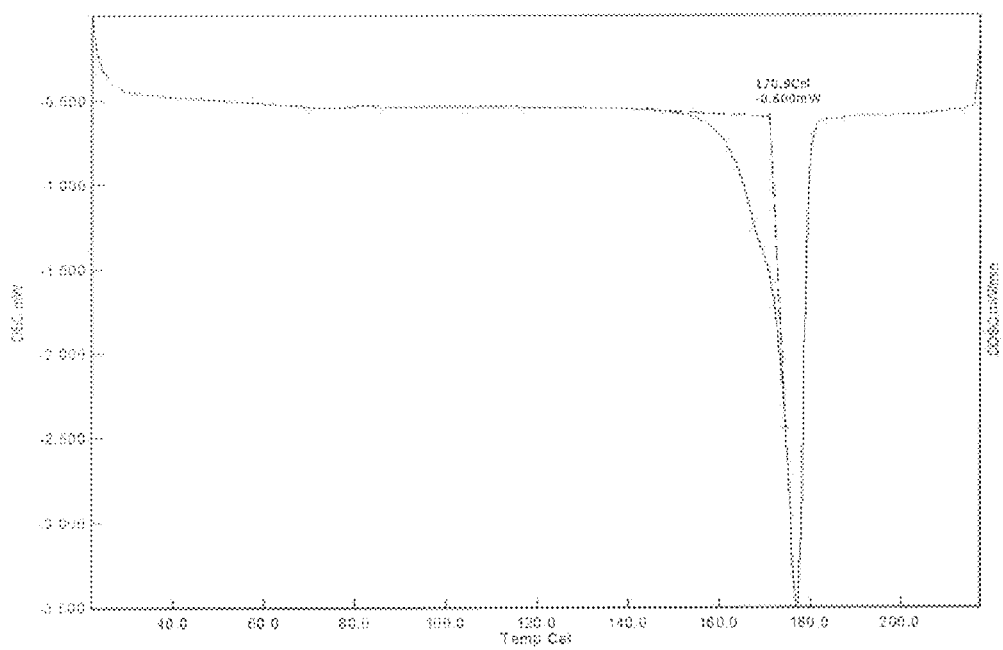
FIG. 2 depicts a differential scanning calorimetry (DSC) trace of the input material of curcumin crystalline.
Figure 3:
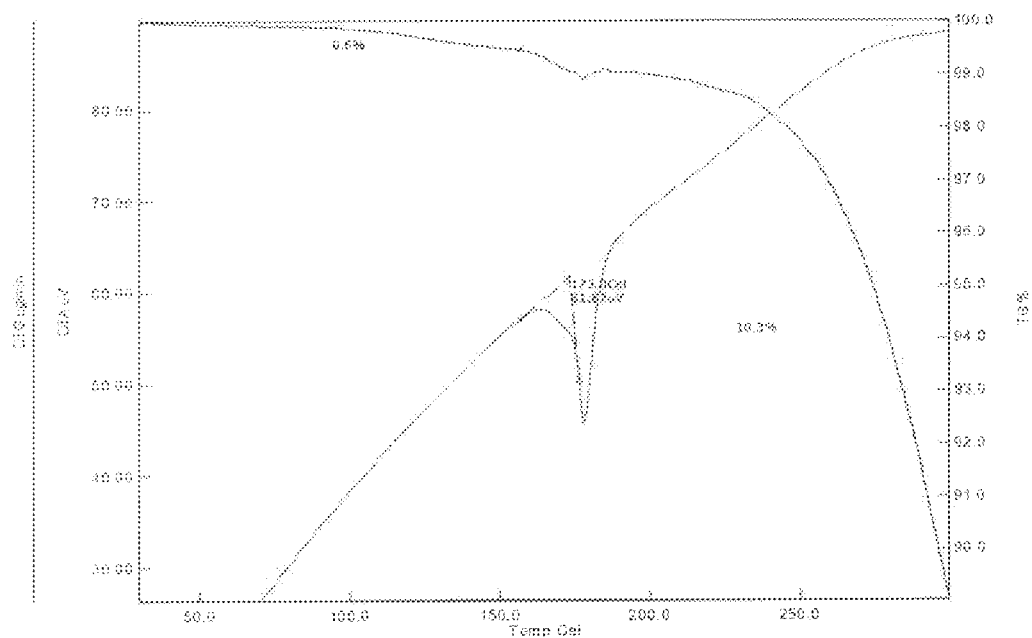
FIG. 3 depicts a thermogravimetric analysis (TGA) trace of the input material of curcumin crystalline.
Figure 4:
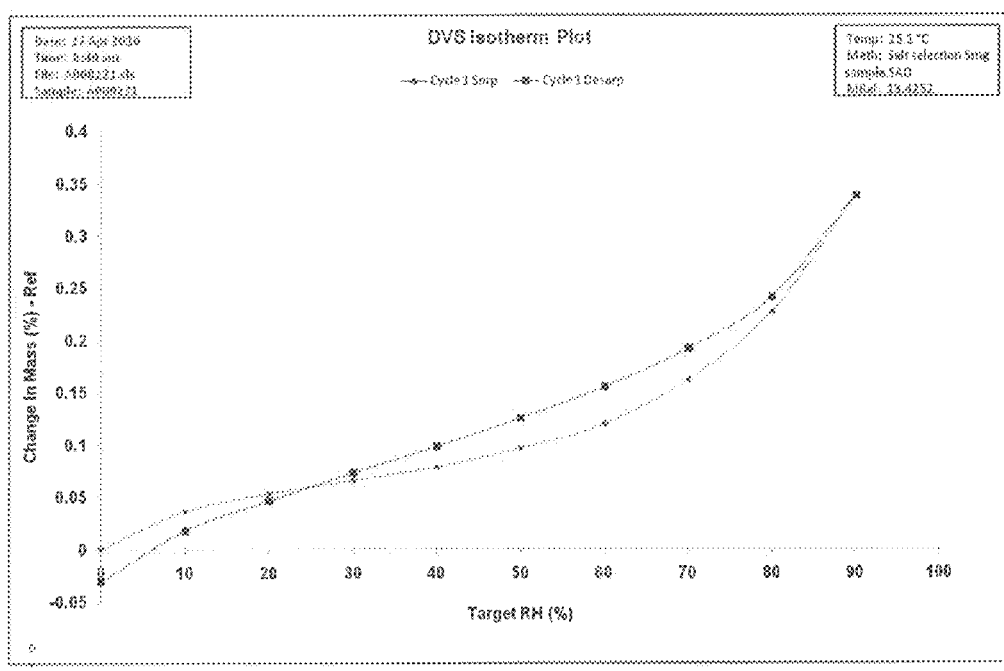
FIG. 4 depicts a dynamic vapor sorption (DVS) trace of the input material of curcumin crystalline.
Figure 5:
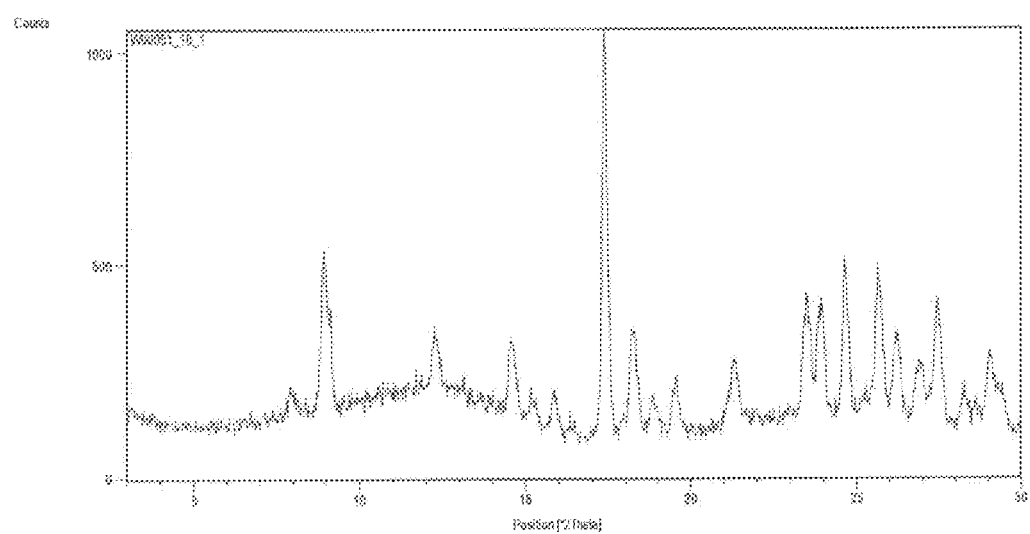
FIG. 5 depicts an X-ray powder diffraction (XRPD) pattern of input material of curcumin crystalline post the dynamic vapor sorption (DVS) analysis. Peak intensity is plotted as a function of degrees 2-theta.

The curcumin input material exhibits an X-ray powder diffraction pattern comprising characteristic peaks expressed in degrees 2-theta as diagrammed in FIG. 1. In particular, the input material exhibits predominant peaks expressed in degrees 2-theta at about 9.28, about 18.56, about 19.15, 24.19, 24.95, 25.93 and about 26.52. The input material also exhibits significant peaks at about 12.62, about 14.92, about 15.52, about 19.83 about 21.60, about 27.15, about 27.70, and about 29.32 in degrees 2-theta. XRPD indicated the material was crystalline. The curcumin input material exhibits a characteristic melting endoderm, as depicted in the differential scanning calorimetry thermogram shown in FIG. 2. In particular, curcumin input material exhibits an endothermic transition with a broad melt at about 170.9° C. as measured by differential scanning calorimetry. Further TGA confirmed that curcumin input material was anhydrous, as only 0.6% small weight loss, as shown in FIG. 3. DVS showed that curcumin input material was not hygroscopic with only a negligible 0.35% water uptake, as shown in FIG. 4. XRPD was performed again after the DVS experiment, and FIG. 5 shows that no polymorphic transformation or degradation occurred as the predominant peaks and other significant peak remain, as shown in FIG. 1 remain. The solubility of curcumin input material was examined in 24 solvents, it was determined to be highly soluble in: DMSO, DMF, 1,4-dioxane, MEK, NMP and THF, and moderately soluble in: acetone, ethyl acetate, methyl acetate and MIBK.

Example 2

Characterization of Curcumin Polymorph Form I

Figure 6:
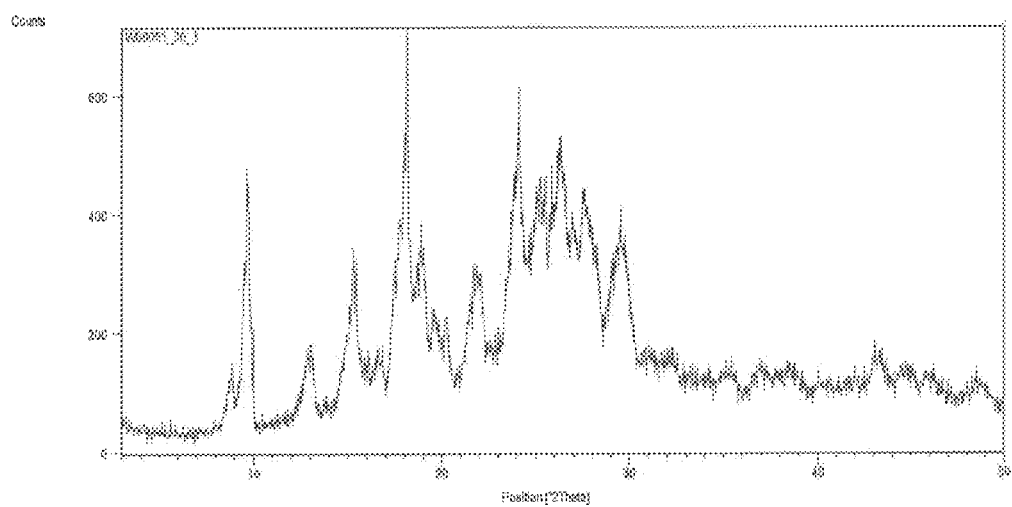
FIG. 6 depicts an X-ray powder diffraction (XRPD) pattern of polymorph Form I of curcumin. Peak intensity is plotted as a function of degrees 2-theta.

Crystalline Form I curcumin exhibits an X-ray powder diffraction pattern comprising characteristic peaks expressed in degrees 2-theta, as diagrammed in FIG. 6. In particular, Form I exhibits predominant peaks expressed in degrees 2-theta at about 9.63, about 18.12, about 24.12, 26.34, 27.58, and about 19.64. Form I also exhibits significant peaks at about 8.87, about 13.08, about 15.28, about 18.98, about 19.62, about 22.06, about 25.40, and about 29.64 in degrees 2-theta. XRPD indicated the material was crystalline.

Figure 7:
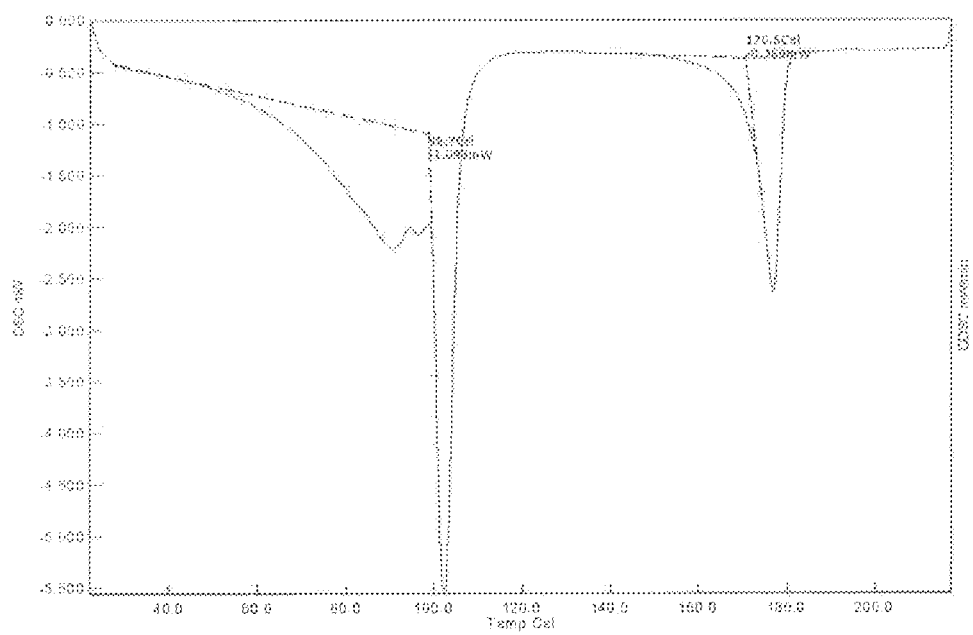
FIG. 7 depicts a differential scanning calorimetry (DSC) trace of polymorph Form I of curcumin.
Figure 8:
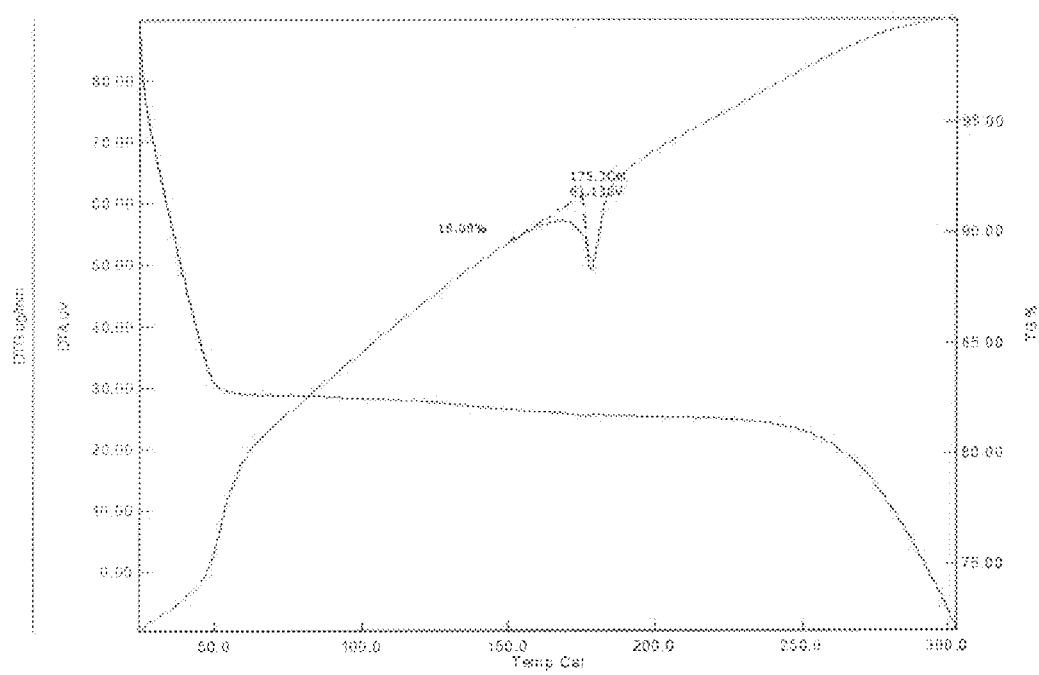
FIG. 8 depicts a thermogravimetric analysis (TGA) trace of polymorph Form I of curcumin after drying under vacuum at 25° C.

Crystalline Form I of curcumin exhibits a characteristic melting endoderm, as depicted in the differential scanning calorimetry thermogram shown in FIG. 7. DSC was carried out immediately after isolation, and several endotherms were observed at 98.7° C., signifying the presence of excess solvent, MEK herein. The polymorph Form I melt was observed at 170.5° C. TGA analysis was carried out immediately after isolation and again after about 72-hour drying under vacuum. The drying process successfully removed the majority of excess free solvent, comparing the 18.1% weight loss without drying (not shown) to 1.4% weight loss with drying (FIG. 8). Further weight loss was observed at degradation (FIG. 8). Small weight loss in TGA analysis confirmed that Form I was anhydrous.

Figure 9:
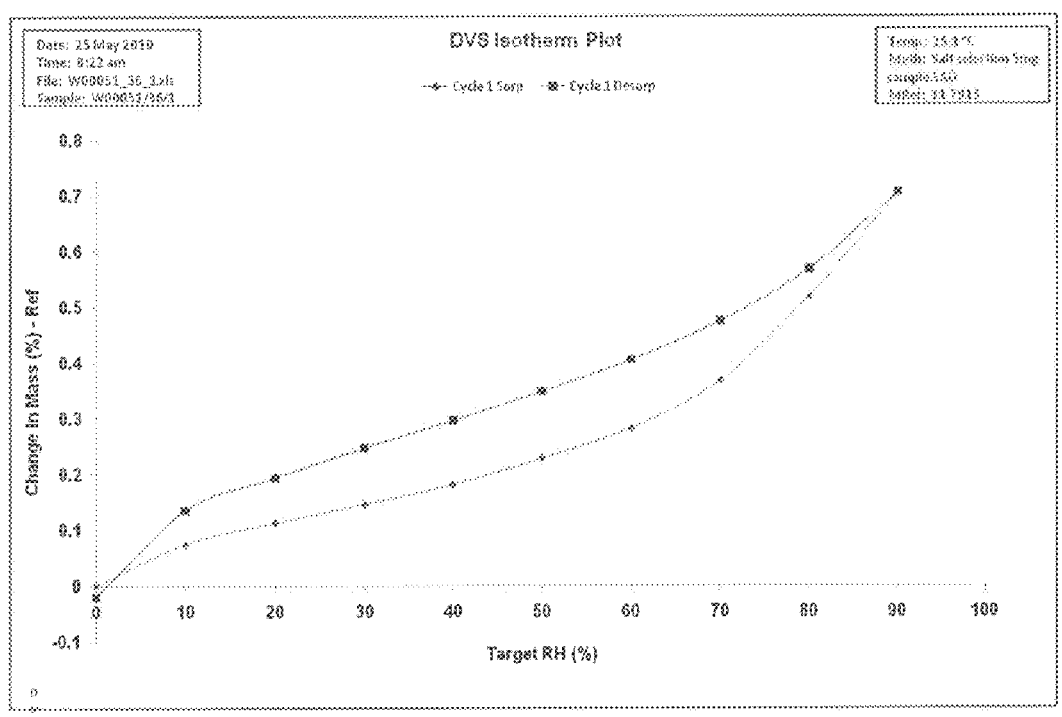
FIG. 9 depicts a dynamic vapor sorption (DVS) trace of polymorph Form I of curcumin.
Figure 10:
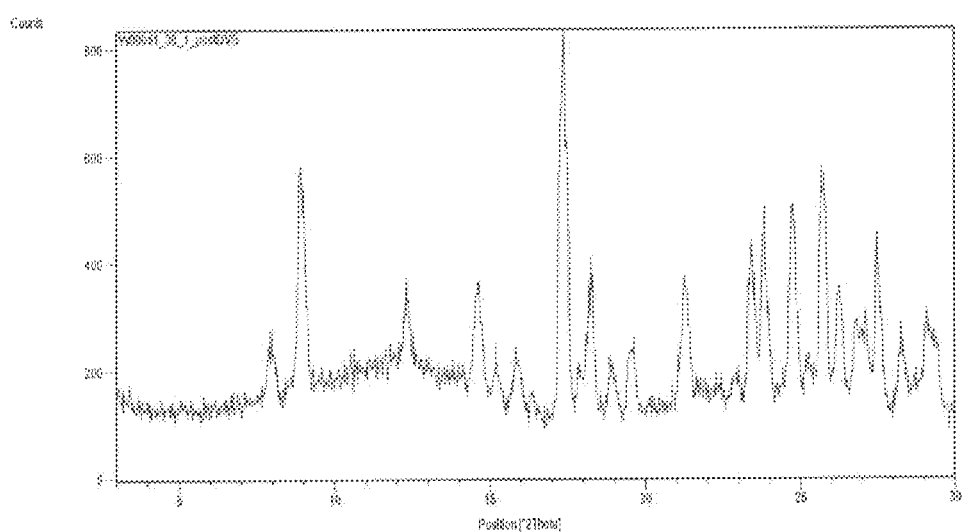
FIG. 10 depicts an X-ray powder diffraction (XRPD) pattern of polymorph Form I of curcumin post the dynamic vapor sorption (DVS) analysis. Peak intensity is plotted as a function of degrees 2-theta.
Figure 11:
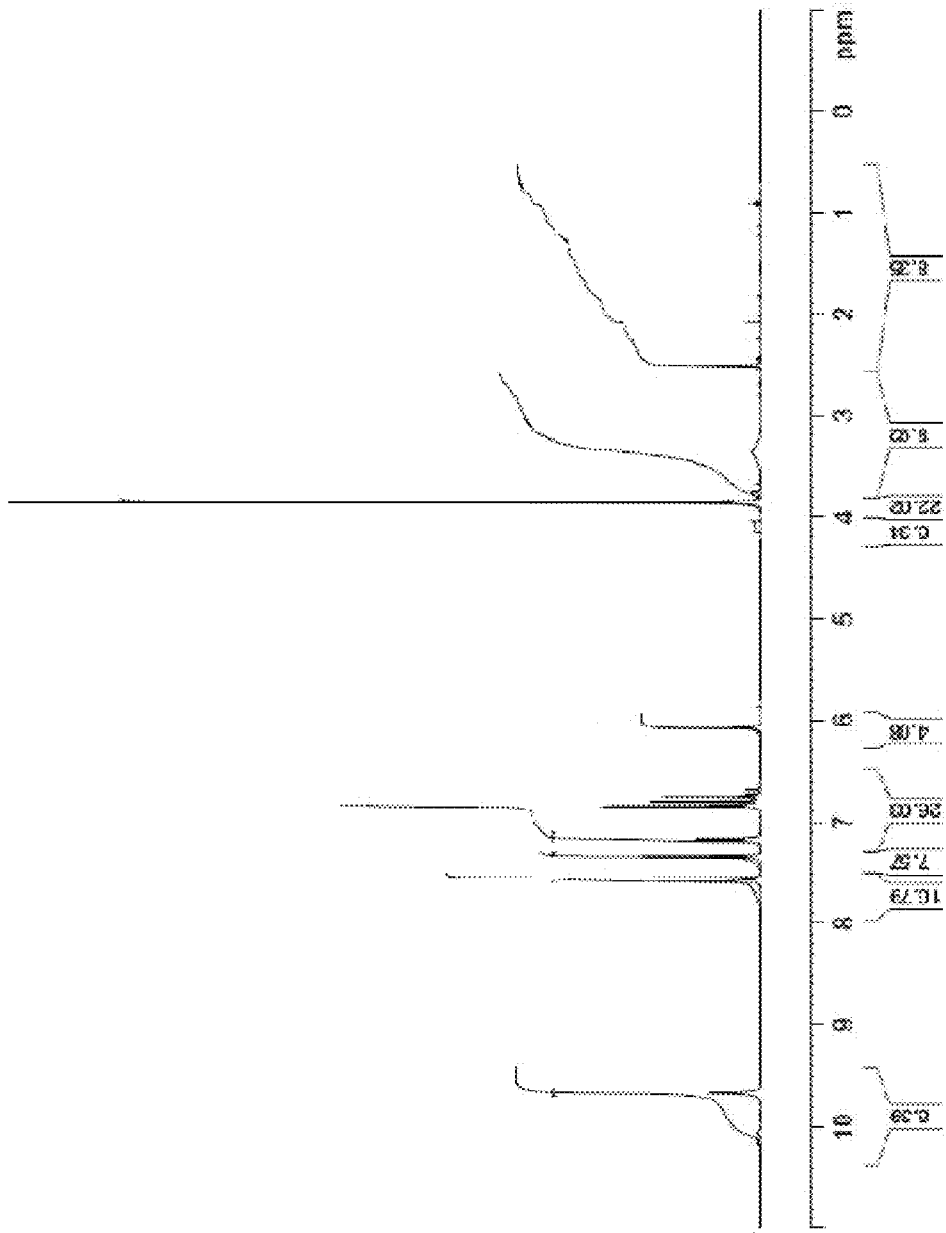
FIG. 11 depicts NMR $^1$H spectrum of polymorph Form I of curcumin. The spectrum integrates to a 1:1 stoichiometry.
Figure 12:
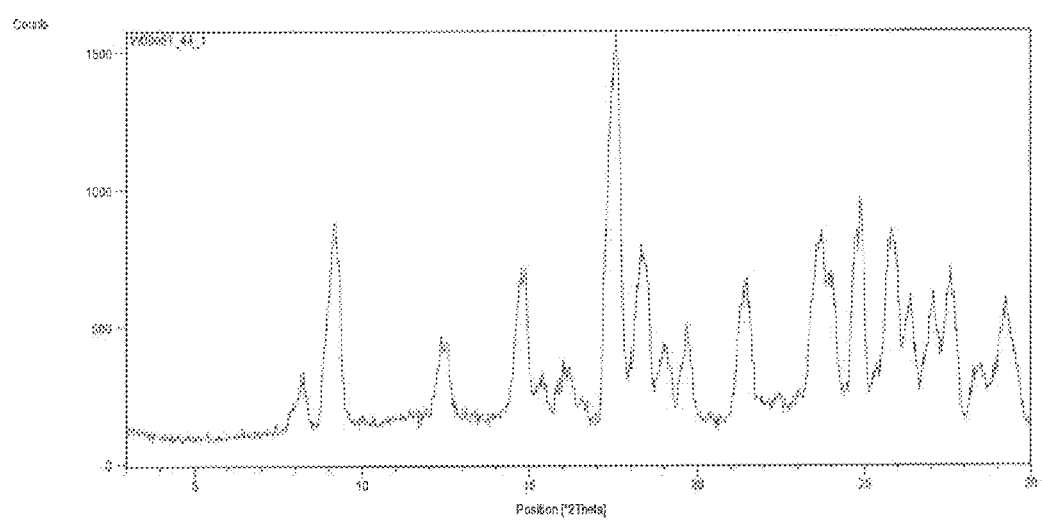
FIG. 12 depicts an X-ray powder diffraction (XRPD) pattern of 80° C. stability test of polymorph Form I of curcumin. Peak intensity is plotted as a function of degrees 2-theta.
Figure 13:
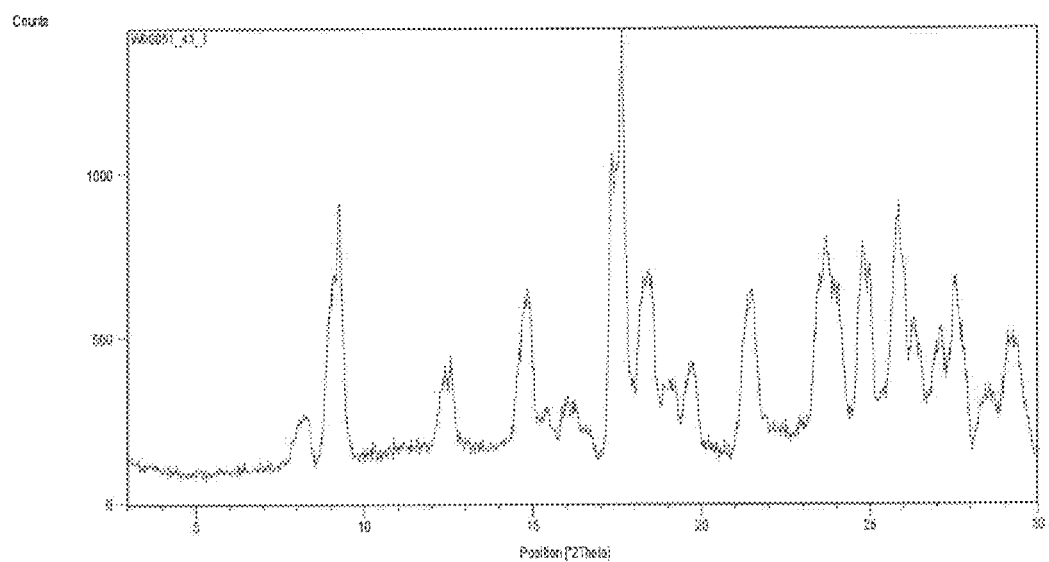
FIG. 13 depicts an X-ray powder diffraction (XRPD) pattern of 40° C./75% RH stability test of polymorph Form I of curcumin. Peak intensity is plotted as a function of degrees 2-theta.

DVS indicated that Form I was not hygroscopic with only a negligible water uptake of 0.7%, and Form I did not retain any of the water as it returned to 0% on the desorption cycle as shown in FIG. 9. XRPD was performed again after the DVS experiment, and FIG. 10 shows that no polymorphic transformation or degradation occurred as the predominant peaks and other significant peak remain, as shown in FIG. 6. NMR confirmed the material was chemically intact (FIG. 11). 80° C. stability test showed the Form I remained the same as indicated by the XRPD diffractogram pattern (FIG. 12). 40° C./75% RH stability test also showed that Form I remained the same as shown by the XRPD diffrectogram pattern (FIG. 13). Aqueous solubility was found to be lower than the LLOQ (<0.3125 Fg/ml). Quantification was not possible as the concentration of curcumin was below the detection limit of the analytical system.

Example 3

Characterization of Curcumin Polymorph Form III

Figure 14:
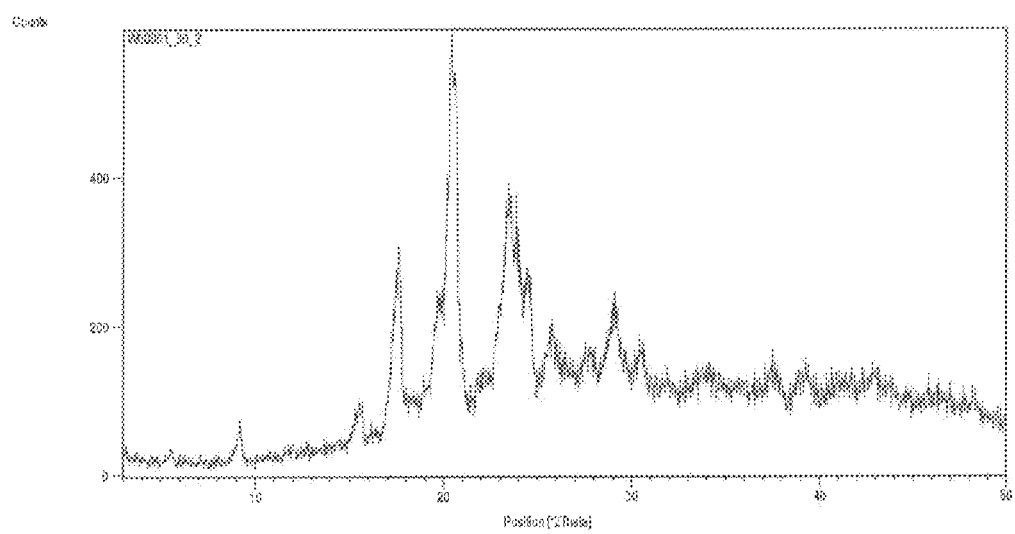
FIG. 14 depicts an X-ray powder diffraction (XRPD) pattern of polymorph Form III of curcumin. Peak intensity is plotted as a function of degrees 2-theta.

Crystalline Form III curcumin exhibits an X-ray powder diffraction pattern comprising characteristic peaks expressed in degrees 2-theta as diagrammed in FIG. 14. In particular, Form III exhibits predominant peaks expressed in degrees 2-theta at about 9.56, about 14.51, about 17.90, and about 26.86. Form I also exhibits significant peaks at about 8.56, about 15.12, about 15.56, about 16.60, about 18.76, about 19.37, about 20.05, about 21.88, about 27.31, about 27.99 and about 28.74 in degrees 2-theta. XRPD indicated Form III was crystalline.

Figure 15:
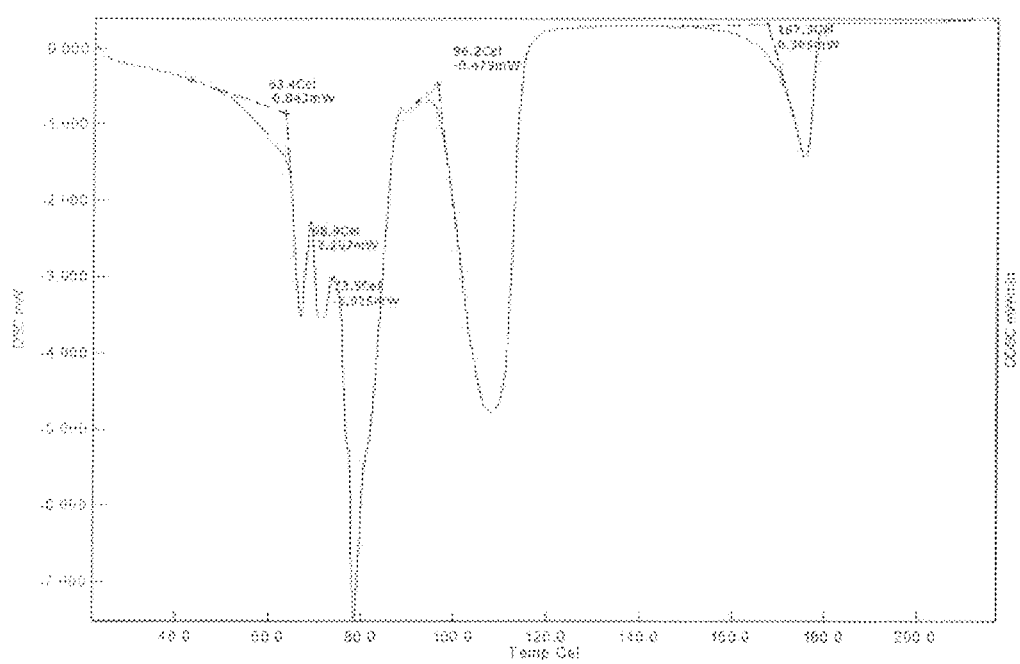
FIG. 15 depicts a differential scanning calorimetry (DSC) trace of polymorph Form III of curcumin.
Figure 16:
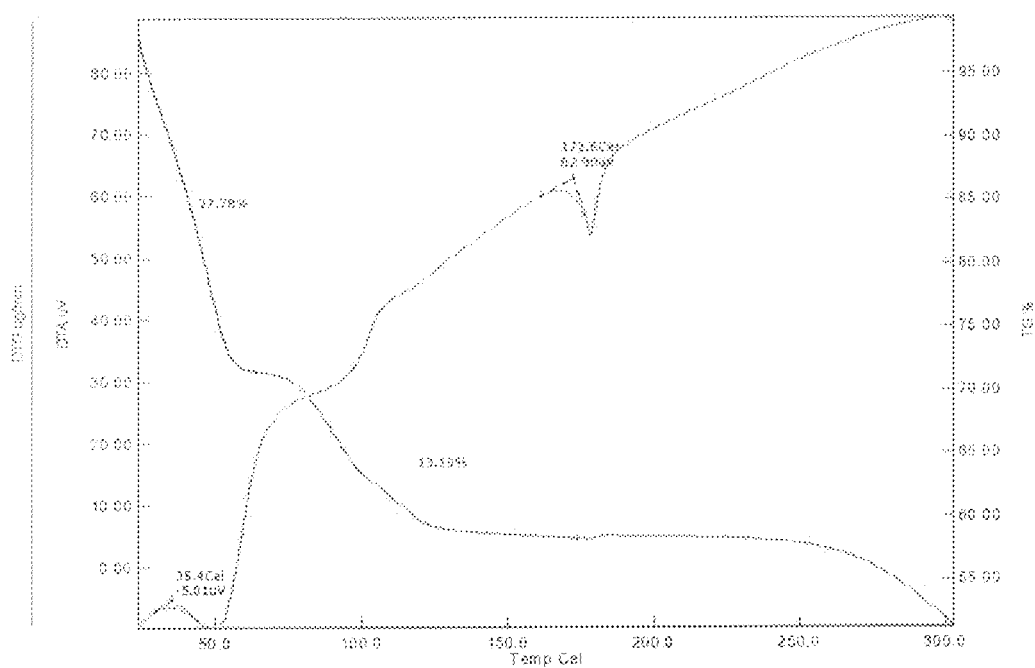
FIG. 16 depicts a thermogravimetric analysis (TGA) trace of polymorph Form III of curcumin after drying under vacuum at 25° C.
Figure 17:
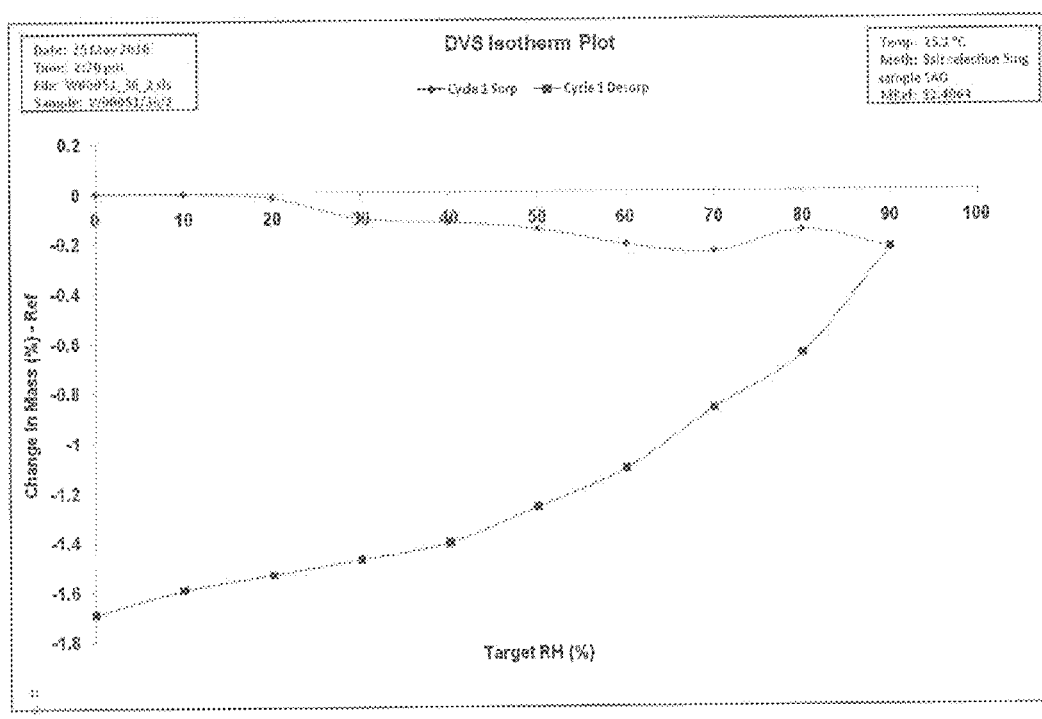
FIG. 17 depicts a dynamic vapor sorption (DVS) trace of polymorph Form III of curcumin.
Figure 18:
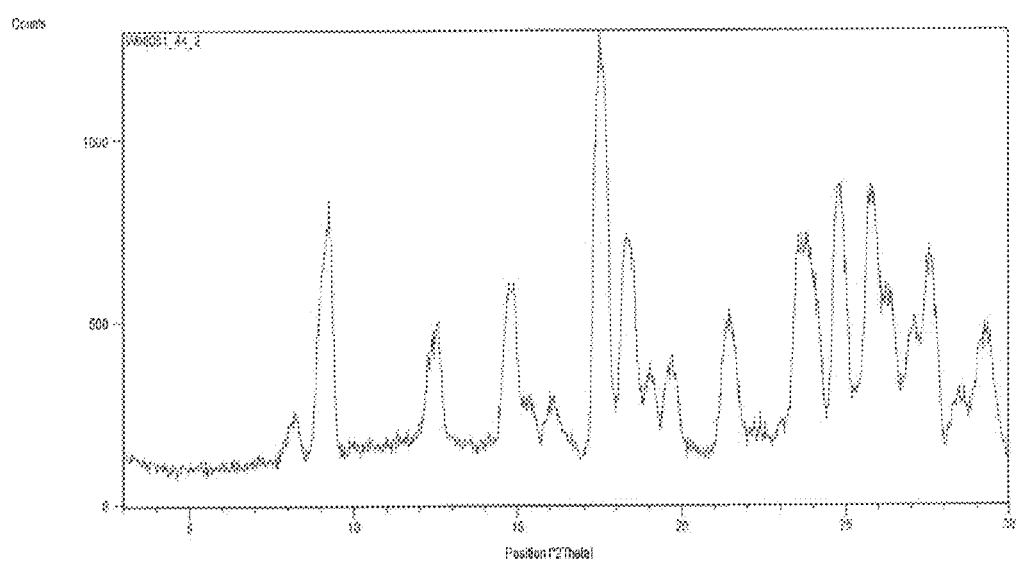
FIG. 18 depicts an X-ray powder diffraction (XRPD) pattern of 80° C. stability test of polymorph Form III of curcumin. Peak intensity is plotted as a function of degrees 2-theta.
Figure 19:
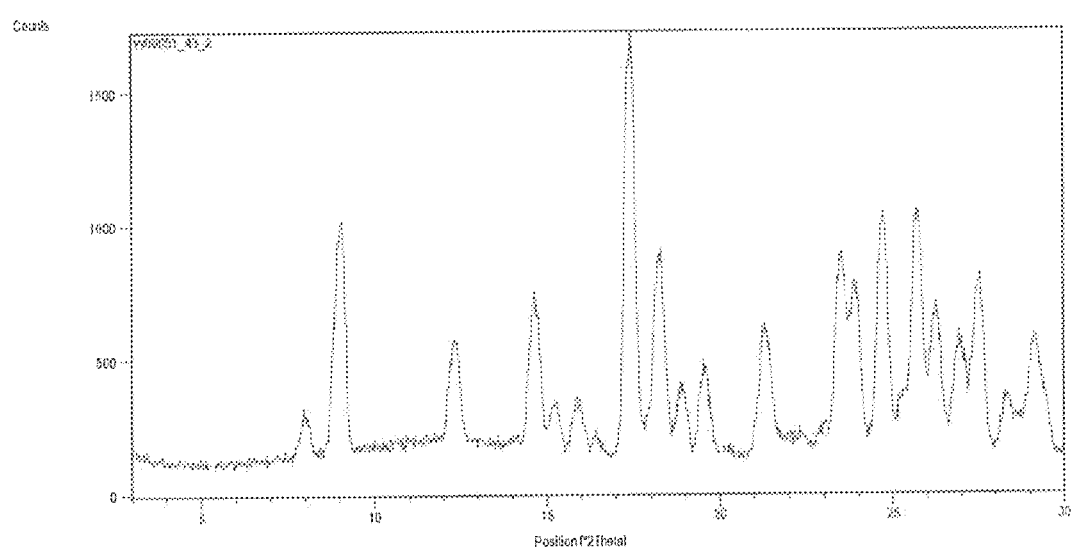
FIG. 19 depicts an X-ray powder diffraction (XRPD) pattern of 40° C./75% RH stability test of polymorph Form III of curcumin. Peak intensity is plotted as a function of degrees 2-theta.

Crystalline Form III of curcumin exhibits a characteristic melting endoderm, which was observed at 162.6° C. as depicted in the differential scanning calorimetry thermogram shown in FIG. 15. Further, TGA confirmed that Form I was anhydrous, as no weight loss was observed as shown in FIG. 16. DVS showed that Form I was not hygroscopic with 4.5% weight loss for the sample being wet, as shown in FIG. 17. XRPD diffractogram of 80° C. stability test showed Form III transformed into Form I, as shown in FIG. 18. Further, XRPD diffrectogram of 40° C./75% RH stability test showed that Form III transformed into Form I as shown in FIG. 19.

Post-DVS XRPD was also performed and there was no polymorphic transformation or degradation occurred as the predominant peaks and other significant peak remain, as in FIG. 14. Quantification of aqueous solubility was not obtained for Form III because the concentration of curcumin was below the detection limit of the analytical system. Although Form III is less stable than Form I, it appears to be more soluble than Form I with respect to dissolution characteristics.

Example 4

Form II has been Identified as a 1,4-Dioxane Solvate

Figure 20:
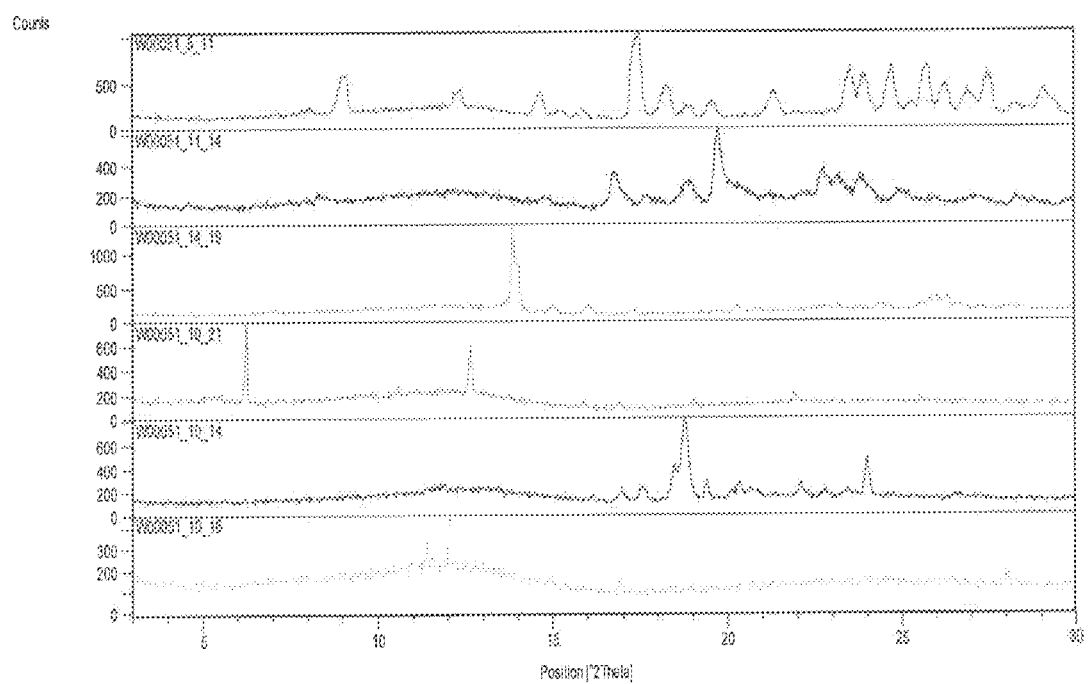
FIG. 20 depicts an representative X-ray powder diffraction (XRPD) pattern of polymorph Form I, II, III IV, V and VI of curcumin. Peak intensity is plotted as a function of degrees 2-theta.

XRPD showed good crystallinity of Form II and the pattern matched previous diffractogram obtained from the primary polymorph screen. A list of peak positions include: 5.55, 9.18, 15.57, 17.66, 19.63, 20.41, 20.64, 23.46, 24.62, 25.70, 29.17, 30.52, 33.85, 37.65, 39.17, 43.13 (FIG. 20). DSC was carried out immediately after isolation several endotherms were present at 63.4, 68.9, 73.5 and 96.2° C. signifying the presence of excess solvent (1,4-dioxane and H2O). The melting point was observed at 167.3° C.

DSC was repeated after about 72 hours of drying under vacuum; however a broad endotherm at 76.0° C. remained, followed by the sample melt at 169.6° C. TGA analysis was carried out immediately after isolation and again after about 72 hrs drying under vacuum, the following weight losses were observed respectively; 27.8% and 13.2%, and 13.4% and 0.8%. This procedure successfully removed the majority of excess free solvent. The solvate, 13.4%, could equate to 0.66 mole of 1,4-dioxane or potentially a mixed solvate/hydrate made up of 0.5 mole of 1,4-dioxane and 1 mole of H2O. Further weight loss was observed at degradation.

KF analysis was carried out on the sample after about 72 hrs drying under vacuum, the water content was found to be 0.327% therefore Form II was unlikely to be a mixed solvate/hydrate. DVS resulted in partial desolvation with a weight loss of about 1.7%. NMR singlet peak at 3.57 ppm confirmed the material was chemically intact and the presence of solvent: 1,4-dioxane. 80° C. stability test showed the material transformed into Form I. Similarly, 40° C./75% RH stability test showed the material transformed into Form I. Aqueous solubility was found to be lower than the LLOQ (<0.3125 Fg/ml).

Example 5

Form V has been Identified as a 1-4-Dioxane Solvate

XRPD showed good crystallinity and matched previous diffractogram obtained from the primary polymorph screen. A list of peak positions include: 6.09, 8.41, 12.40, 13.71, 17.64, 18.88, 19.39, 20.87, 22.76, 24.17, 24.70, 27.22, 29.28, 31.09, 32.22, 34.14, 35.96, 37.56, 39.17, 40.69, 42.84, 48.08 (FIG. 20). DSC was carried out immediately after isolation, and there were several endotherms present at 81.5° C. and 106.9° C., signifying the presence of excess solvent (1,4-dioxane) in the free and bound form, in correspondence with the TGA data. The melting point was at 143.7° C.

DSC was carried out again after about 72 hours drying under vacuum, several endotherms were present at 78.6° C. and 99.1° C. signifying the presence of excess solvent (1,4-dioxane) free and bound. The sample melt after drying was observed at 177.2° C. TGA analysis was carried out immediately after isolation and again after ca. 72 hrs drying under vacuum, the following weight losses were observed respectively: 4.2, 5.9, 9.0 and 8.5%, and 23.6%. This successfully removed the some of the excess solvent (approximately 4%). The solvate, 23.6%, could equate to 1.25 moles of 1,4-dioxane. Further weight loss was observed at degradation. DVS resulted in partial desolvation with a weight loss of approximately 15%.

NMR confirmed the material was chemically intact and the presence of solvent 1,4-dioxane represented by a singlet peak at 3.57 ppm. 80° C. stability test showed the material transformed into Form I. 40° C./75% RH stability test showed the material transformed into Form I as well. Aqueous solubility was found to be lower than the LLOQ (<0.3125 Fg/ml). Quantification of the solubility was not possible as the concentration of curcumin was below the detection limit of the analytical system.

Example 6

Form VI has been Identified as a Methyl Acetate Solvate

XRPD showed good crystallinity of Form VI and the pattern matched previous diffractogram obtained from the primary polymorph screen. A list of peak positions include: 9.08, 12.11, 12.78, 13.25, 15.02, 15.73, 16.06, 16.69, 17.34, 17.83, 18.58, 19.70, 20.62, 21.06, 23.22, 24.10, 24.66, 25.05, 25.24, 25.96, 26.77, 27.08, 27.28, 29.57, 30.69, 32.03, 33.62, 34.67, 35.95, 41.27, 42.60, 44.09, 46.21, and 47.58 (FIG. 20). DSC was carried out immediately after isolation, and several endotherms were present at 46.3° C., signifying the presence of excess solvent, methyl acetate. The sample melt was observed at 176.0° C. DSC was carried out again after about 72 hours of drying under vacuum, and the sample melt was observed at 176.2° C.

TGA analysis was carried out immediately after isolation and again after about 72 hrs drying under vacuum, the 28.5% and 0.4%. On drying under vacuum, this form desolvates as 28.5% equates to 2 moles methyl acetate. DVS indicated the material was not hygroscopic with only a negligible water uptake of 0.16%, and the sample did not retain any of the water as it returned to 0% on the desorption cycle. NMR confirmed that the material was chemically intact. 80° C. stability test showed the Form VI material transformed into Form I. Similarly, 40° C./75% RH stability test showed the material transformed into Form I. Aqueous solubility was found to be lower than the LLOQ (<0.3125 Fg/ml), and thus the quantification was not possible.

Example 7

Characterization of Curcumin-2-Aminobenzimidazole Co-Crystal

The co-crystallization may use 2-aminobenzimidazole as a co-crystal former. The resulting form, curcumin-2-aminobenzimidazole, is an anhydrous co-crystal that is non-hygroscopic. Curcumin-2-aminobenzimidazole is stable under a range of conditions; temperature, humidity, ambient light and water, with no signs of degradation, disproportionation or loss of crystallinity.

Figure 21:
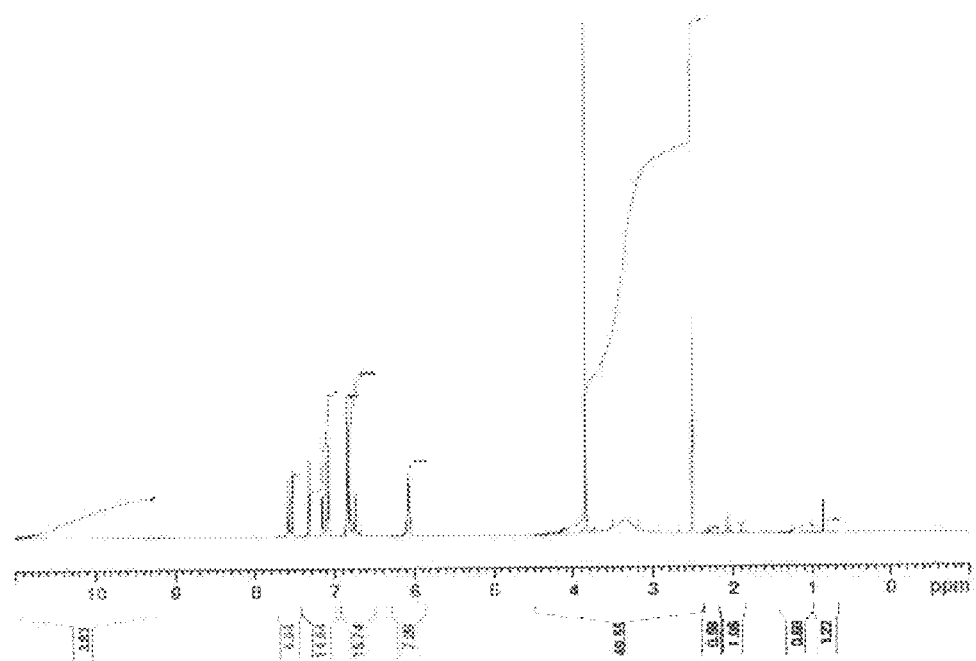
FIG. 21 depicts NMR $^1$H spectrum of curcumin co-crystal curcumin-2-aminobenzimidazole. The spectrum integrates to a 1:1 stoichiometry.
Figure 22:
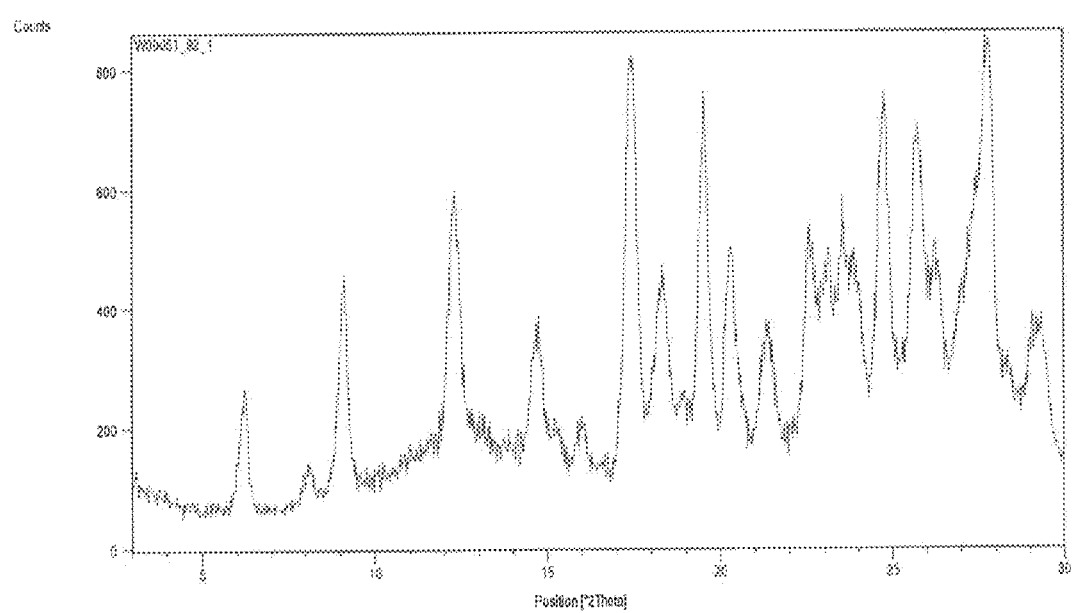
FIG. 22 depicts an X-ray powder diffraction (XRPD) pattern of curcumin co-crystal curcumin-2-aminobenzimidazole. Peak intensity is plotted as a function of degrees 2-theta.
Figure 23:
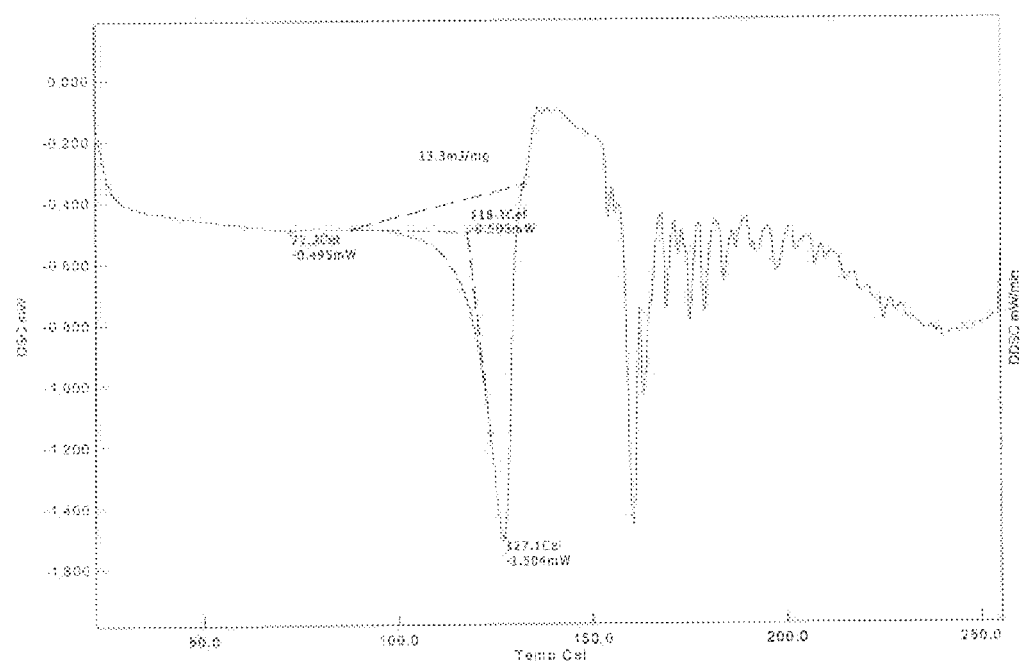
FIG. 23 depicts a differential scanning calorimetry (DSC) trace of curcumin co-crystal curcumin-2-aminobenzimidazole.

The $^1$H NMR confirmed co-crystal formation was successful. The aromatic protons of the 2-aminobenzimidazole are accounted for by peaks at 7.1 ppm (FIG. 21). The spectrum integrates to a 1:1 stoichiometry (FIG. 21). Curcumin-2-aminobenzimidazole exhibits an X-ray powder diffraction pattern comprising characteristic peaks expressed in degrees 2-theta, as diagrammed in FIG. 22. X-ray powder diffraction pattern of curcumin-2-aminobenzimidazole exhibits characteristic peaks expressed in degrees 2-theta at about 6.2, about 9.0, about 12.3, about 14.5, about 17.3, about 18.0, about 19.0, about 20.0, about 21.2, about 24.5, about 25.05, and about 27.1. XRPD indicated the material was crystalline. Crystalline Form I of curcumin exhibits a characteristic melting endoderm, as depicted in the differential scanning calorimetry thermogram shown in FIG. 23. The melting point of curcumin polymorph Form III is 170.9° C. The melting point of co-former, 2-aminobenzimidazole, is 229° C. In comparison, the melting point of curcumin-2-aminobenzimidazole co-crystal is 118° C., as shown in FIG. 23.

Figure 24:
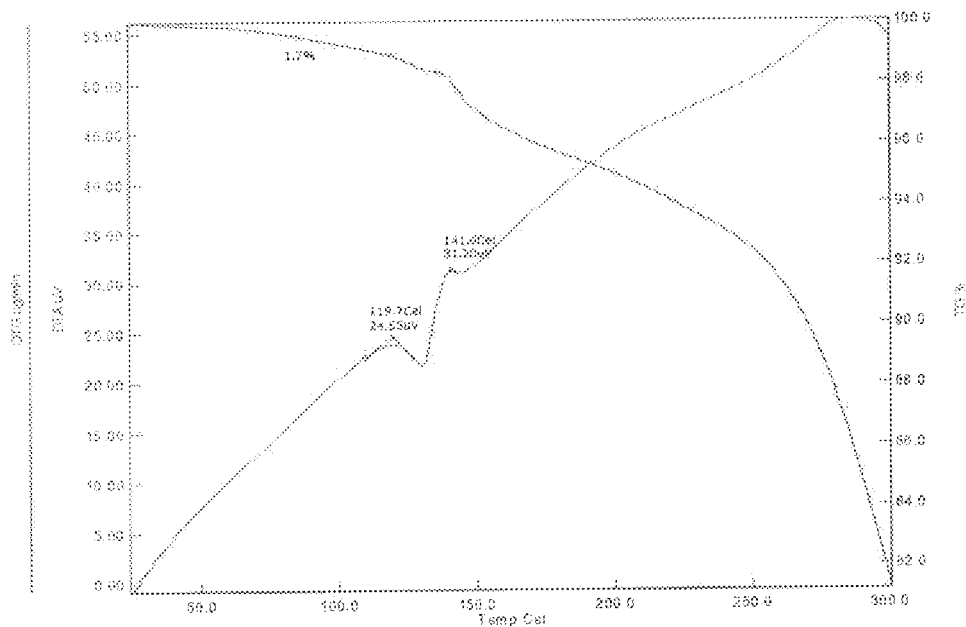
FIG. 24 depicts a thermogravimetric analysis (TGA) trace of curcumin co-crystal curcumin-2-aminobenzimidazole after drying under vacuum at 25° C.
Figure 25:
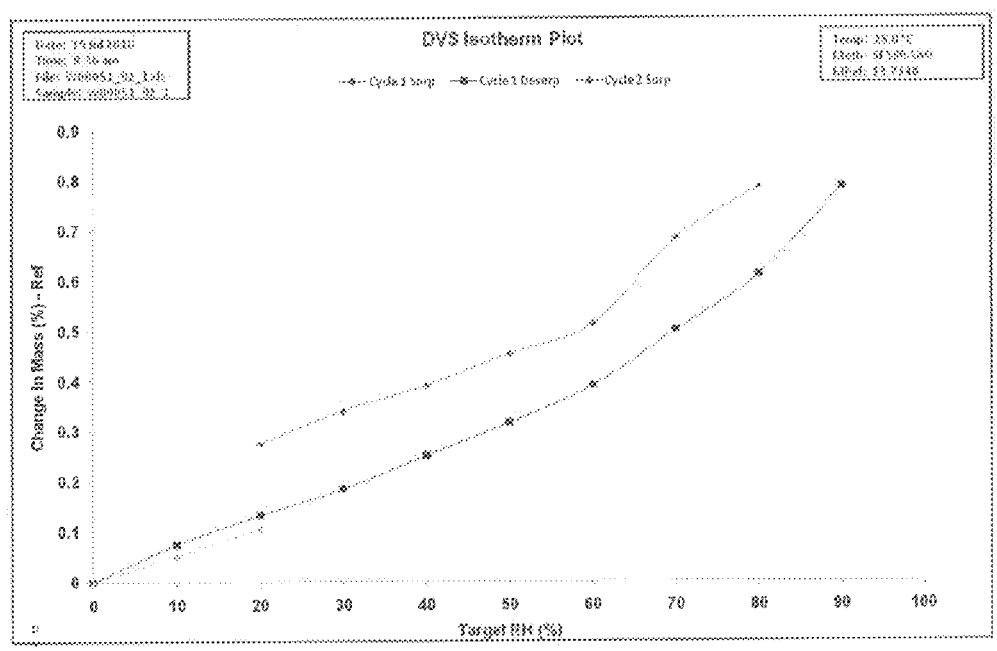
FIG. 25 depicts a dynamic vapor sorption (DVS) trace of curcumin co-crystal curcumin-2-aminobenzimidazole.
Figure 26:
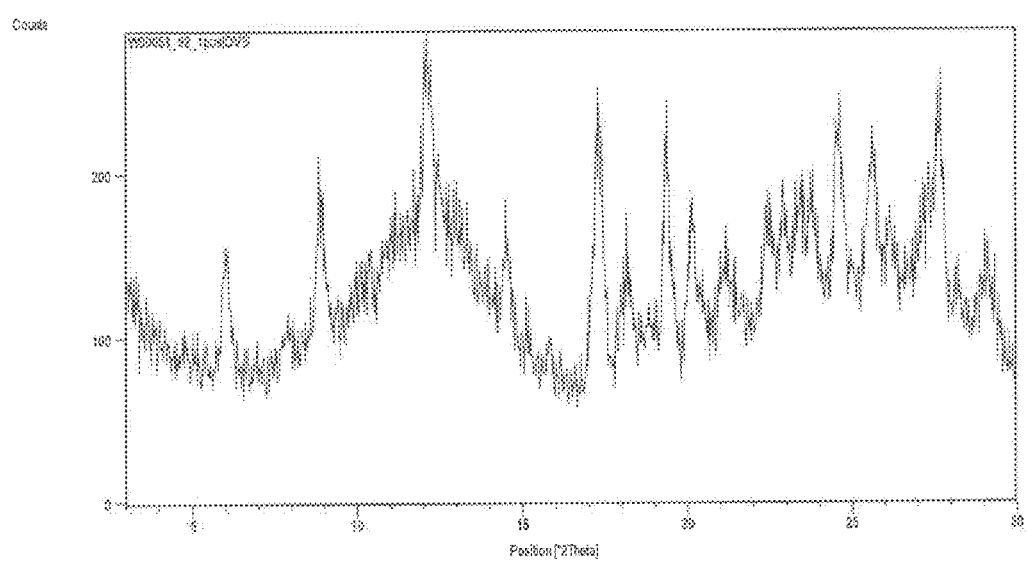
FIG. 26 depicts an X-ray powder diffraction (XRPD) pattern of curcumin co-crystal curcumin-2-aminobenzimidazole post the dynamic vapor sorption (DVS) analysis. Peak intensity is plotted as a function of degrees 2-theta.

Further TGA confirmed that curcumin-2-aminobenzimidazole was anhydrous, as only 1.7% small weight loss as shown in FIG. 24. The weight loss was most likely due to excess solvent from the preparation method—solvent drop grinding using MIBK. DVS showed that curcumin-2-aminobenzimidazole was not hygroscopic with only a negligible water uptake of 0.8%, as shown in FIG. 25. Further the sample of curcumin-2-aminobenzimidazole only retained 0.2% water on the desorption cycle, which was also negligible. Analysis by XRPD post the DVS experiment confirmed no degradation or transformation had occurred (FIG. 26).

Figure 27A:
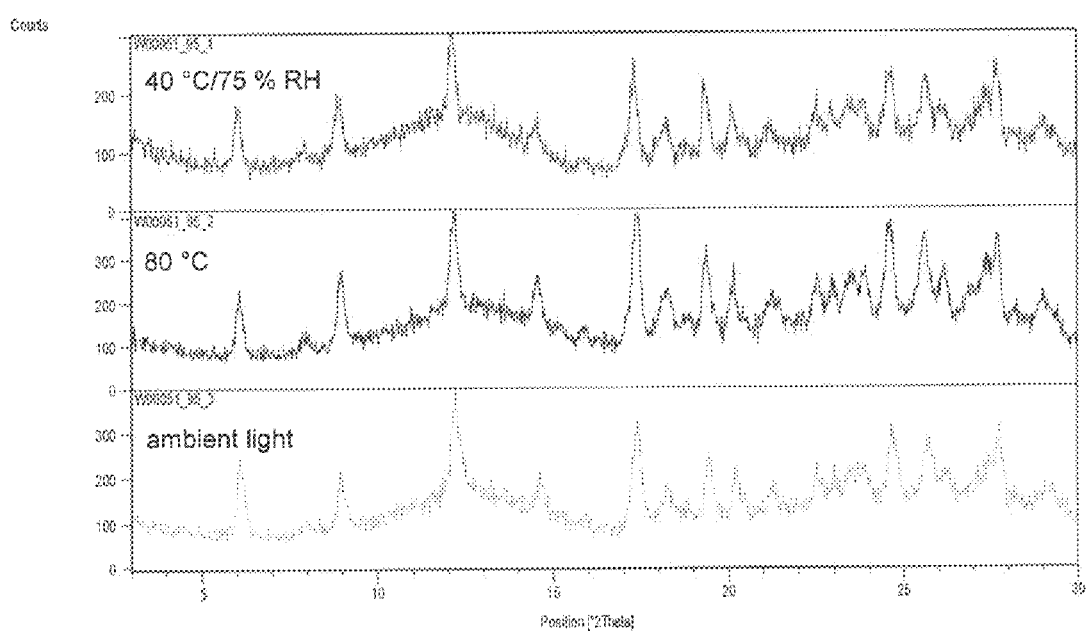
FIG. 27 depicts an X-ray powder diffraction (XRPD) pattern of curcumin co-crystal curcumin-2-aminobenzimidazole of (A) stability tests under 40° C./75% RH; 80° C.; and ambient light; of (B) slurrying in water. Peak intensity is plotted as a function of degrees 2-theta.
Figure 27B:
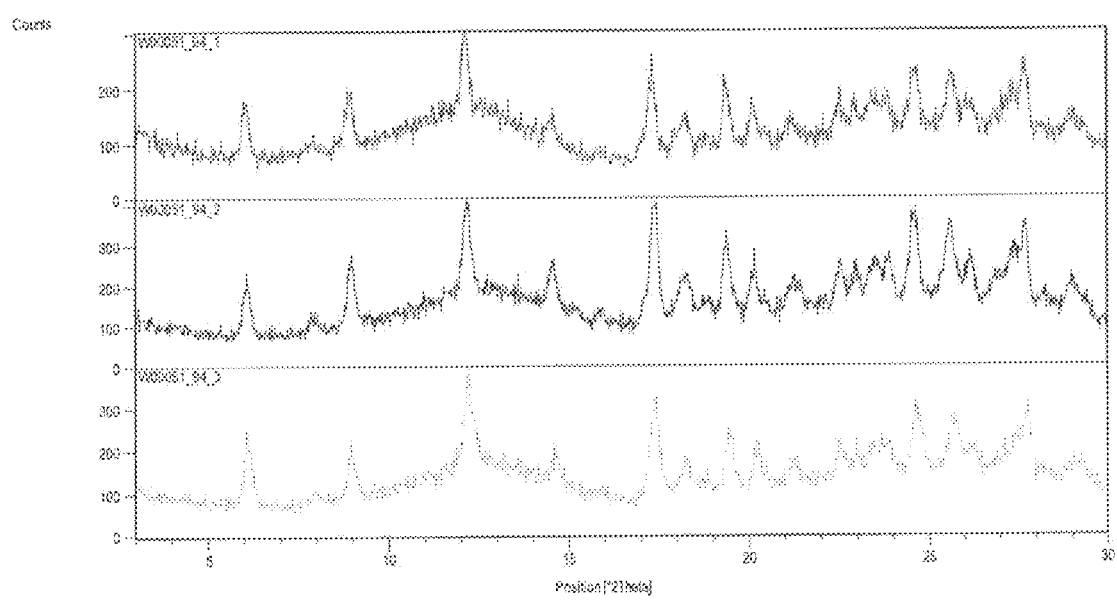

All stability and slurrying in water experiments matched with primary material, so there were no signs of form transformation, disproportionation, degradation or loss in crystallinity (FIGS. 27a and 27b). The intrinsic dissolution rate of curcumin-2-aminobenzimidazole is 0.023, as shown in Table 1.

TABLE 1

Curcumin-2-Aminobenzimidazole co-crystal dissolution data

| Timepoint (min) | Concentration (mg/ml) | Dissolution Rate (mg/min/cm$^2$) | % Dissolved |
|---|---|---|---|
| 1 | <LLOQ | <LLOQ | N/A |
| 5 | 1.773 | 1.002 | 0.869 |
| 10 | 1.934 | 1.093 | 0.949 |
| 15 | 2.026 | 1.145 | 0.994 |
| 30 | 2.787 | 1.575 | 1.367 |
| 60 | 4.329 | 2.446 | 2.123 |
| 120 | 5.189 | 2.932 | 2.545 |
| 240 | 7.371 | 4.165 | 3.616 |
| 1440 | 28.412 | 16.054 | 13.936 |

| Wafer mass (mg) | 115.200 |
|---|---|
| Intrinsic Dissolution Rate | 0.023 |

Example 8

Characterization of Curcumin-Nicotinamide Co-Crystal

The resulting form, curcumin-nicotinamide is an anhydrous co-crystal that is moderately/highly hygroscopic. The preparation method is not fully robust as free API and co-former were still present. The stability of the material was good under a range of conditions: temperature, humidity and ambient light, with no signs of degradation or disproportionation, however when slurrying in water a loss of crystallinity was observed.

Figure 28:
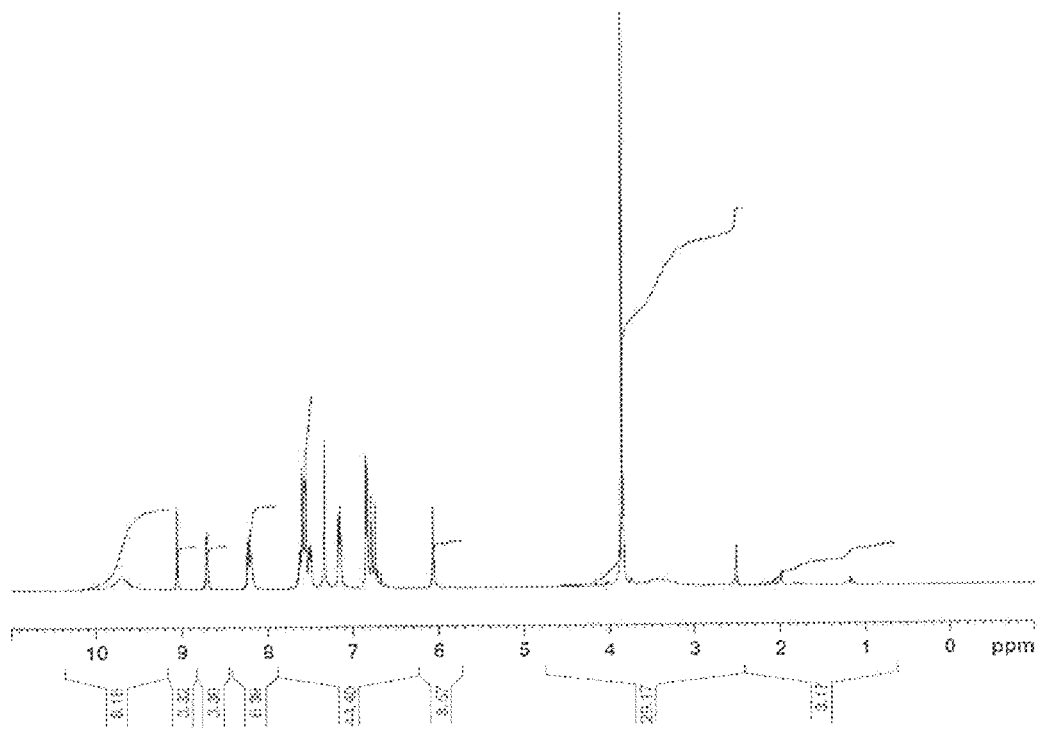
FIG. 28 depicts NMR $^1$H spectrum of curcumin co-crystal curcumin-nicotinamide. The spectrum integrates to a 1:1 stoichiometry.
Figure 29:
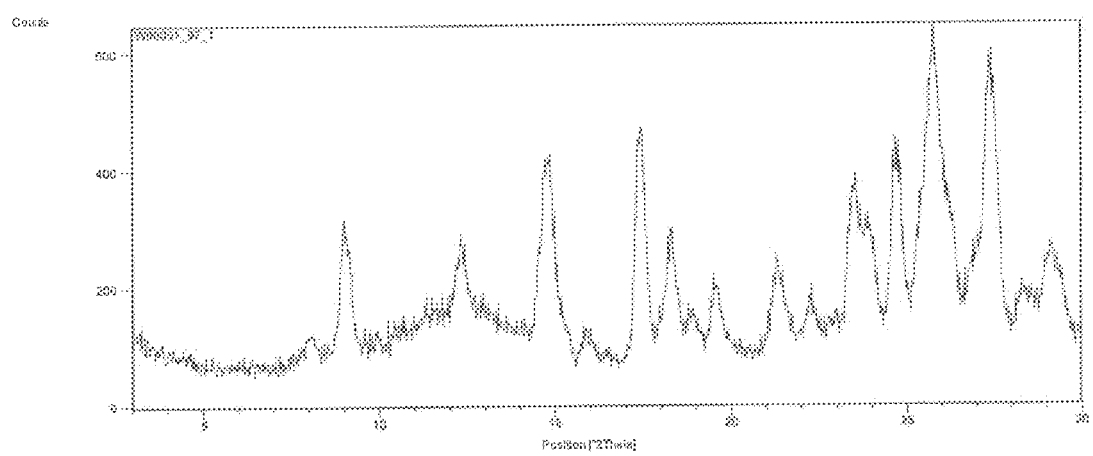
FIG. 29 depicts an X-ray powder diffraction (XRPD) pattern of curcumin co-crystal curcumin-nicotinamide. Peak intensity is plotted as a function of degrees 2-theta.
Figure 30:
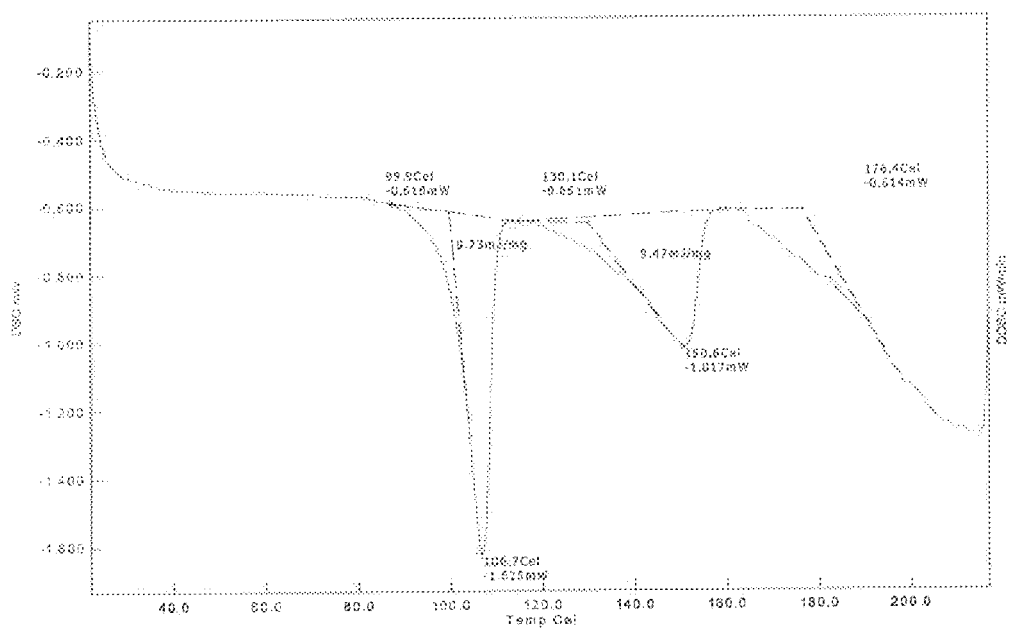
FIG. 30 depicts a differential scanning calorimetry (DSC) trace of curcumin co-crystal curcumin-nicotinamide.

The $^1$H NMR confirmed co-crystal formation was successful with an upfield shift of two peaks at 9.5-10.5 ppm, and this was due to hydrogen bonding effects. The aromatic protons of the nicotinamide are accounted for by peaks in the region of 7.5-8.8 ppm, and the spectrum almost integrates to a 1:1 stoichiometry (FIG. 28). Curcumin-nicotinamide exhibits an X-ray powder diffraction pattern comprising characteristic peaks expressed in degrees 2-theta as diagrammed in FIG. 29 at about 9.0, about 12.2, about 15.0, about 17.5, about 18.5, about 23.5, about 24.5, about 25.4 and about 27.2. XRPD indicated good crystalline and presence of some peaks which were a match to primary screen material (FIG. 29). In correspondence with the DSC data (FIG. 30), presence of free API can also be seen. Curcumin-nicotinamide exhibits a characteristic melting endoderm, as depicted in the differential scanning calorimetry thermogram shown in FIG. 30. The melting point of curcumin polymorph Form III is 170.9° C. The melting point of co-former, nicotinamide, is 128° C. In comparison, the melting point of curcumin-nicotinamide co-crystal is 99.9° C. as shown in FIG. 30.

Figure 31:
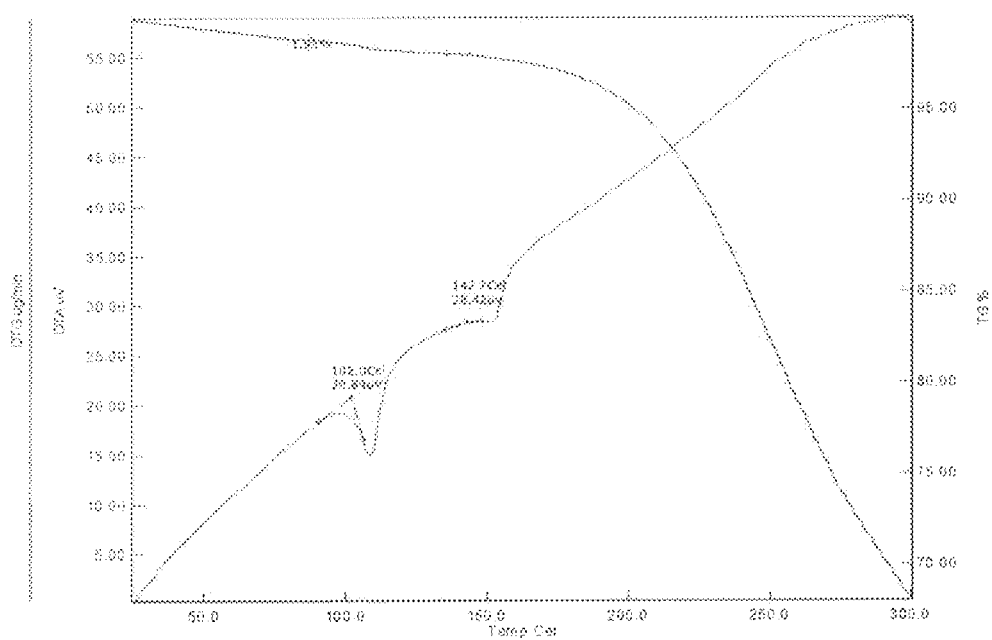
FIG. 31 depicts a thermogravimetric analysis (TGA) trace of curcumin co-crystal curcumin-nicotinamide.
Figure 32:
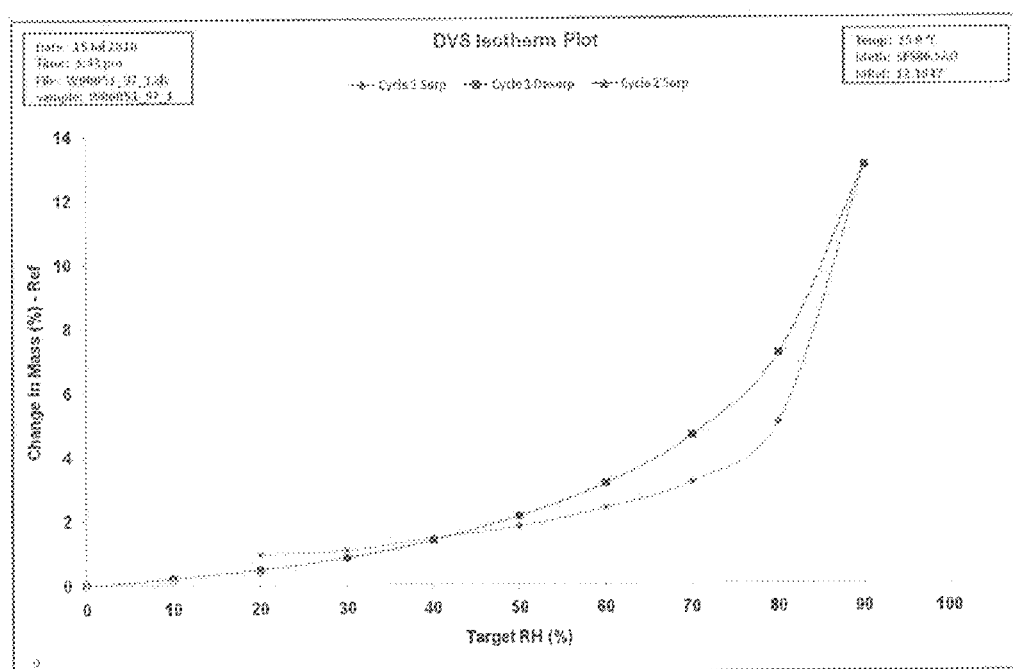
FIG. 32 depicts a dynamic vapor sorption (DVS) trace of curcumin co-crystal curcumin-nicotinamide.
Figure 33:
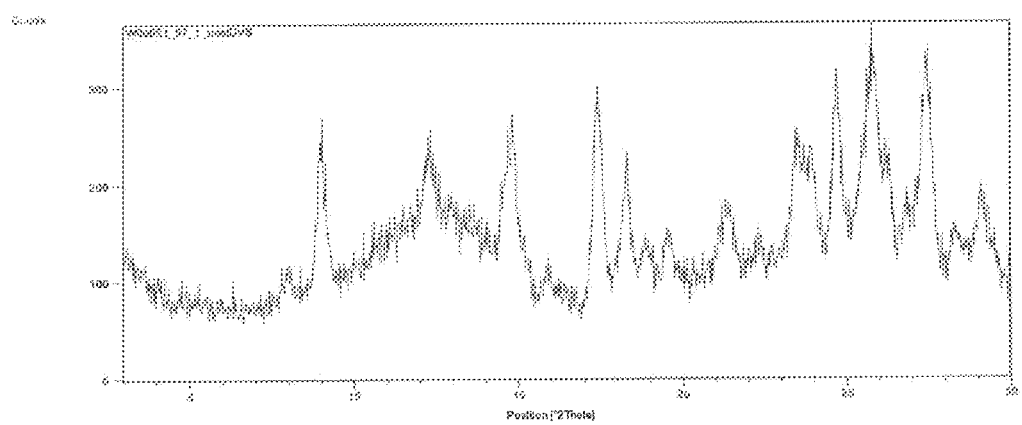
FIG. 33 depicts an X-ray powder diffraction (XRPD) pattern of curcumin co-crystal curcumin-nicotinamide post the dynamic vapor sorption (DVS) analysis. Peak intensity is plotted as a function of degrees 2-theta.

Further TGA confirmed that curcumin-nicotinamide was anhydrous, with a small weight loss of 1.95% as shown in FIG. 31. The weight loss is not an indication of a solvate formation but most likely was due to excess solvent from the preparation method—solvent drop grinding using ethyl acetate. DVS shown in FIG. 32 found that curcumin-nicotinamide co-crystal was moderately hygroscopic (about 13% water uptake), however between the region of 20-70% RH, which is a typical range the material could be exposed to, there is only about 5% water uptake. Analysis by XRPD post the DVS experiment confirmed no degradation or transformation had occurred (FIG. 33).

Figure 34A:
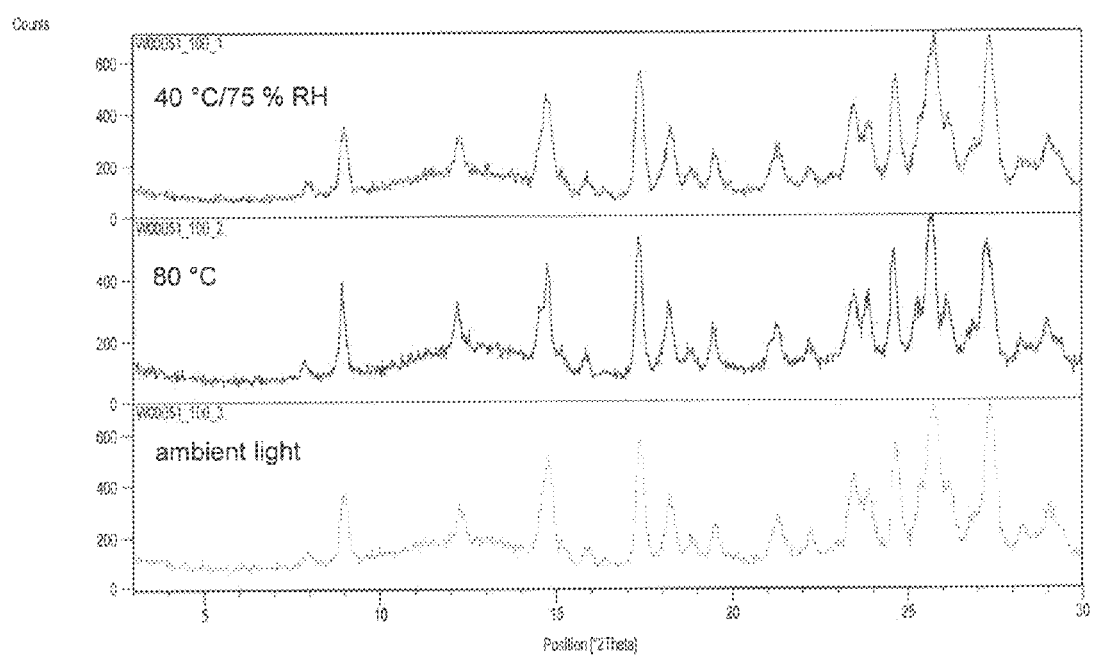
FIG. 34 depicts an X-ray powder diffraction (XRPD) pattern of curcumin co-crystal curcumin-nicotinamide of (A) stability tests under 40° C./75% RH; 80° C.; and ambient light; of (B) slurrying in water. Peak intensity is plotted as a function of degrees 2-theta.
Figure 34B:
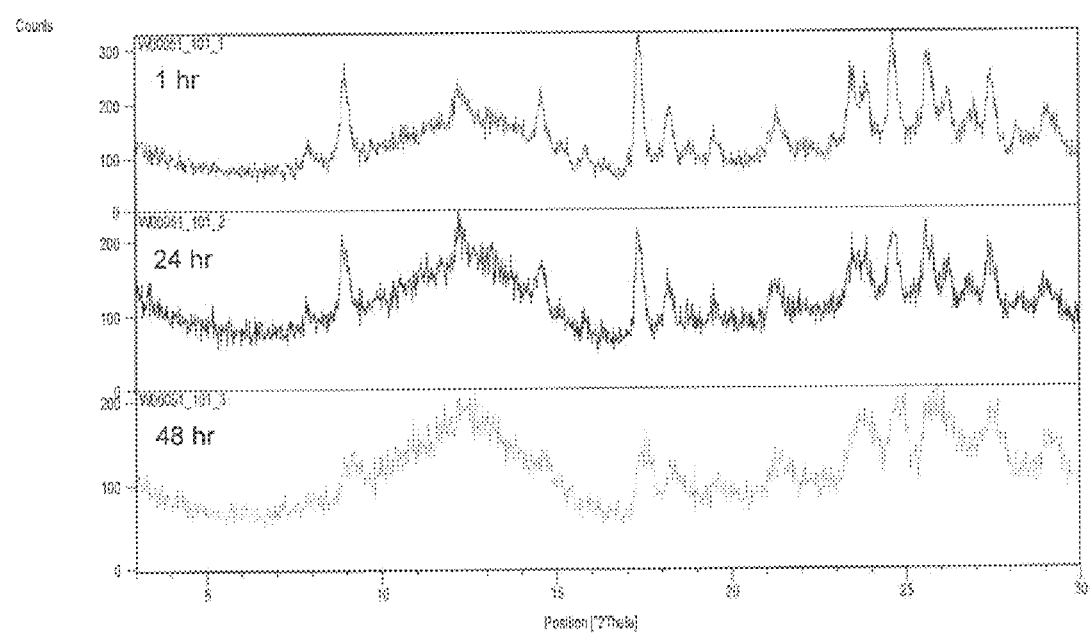

All stability and slurrying in water experiments with curcumin-nicotinamide matched with primary material, showing no signs of form transformation, disproportionation, degradation (FIGS. 34a and 34b). However, a loss in crystallinity was observed as the time points increased of the slurrying in water experiment (FIG. 34b). The intrinsic dissolution rate of curcumin-nicotinamide is 0.040 was approximately two times greater than that of the curcumin-2-aminobenzimidazole co-crystal and is, therefore superior. The intrinsic dissolution rate is shown in Table 2.

TABLE 2

Curcumin-nicotinamide co-crystal dissolution data

| Timepoint (min) | Concentration (mg/ml) | Dissolution Rate (mg/min/cm$^2$) | % Dissolved |
|---|---|---|---|
| 1 | <LLOQ | <LLOQ | N/A |
| 5 | 2.086 | 1.18 | 0.66 |
| 10 | 2.871 | 1.622 | 0.906 |
| 15 | 3.545 | 2.003 | 1.119 |
| 30 | 5.403 | 3.053 | 1.705 |
| 60 | 8.370 | 4.730 | 2.642 |
| 120 | 11.119 | 6.283 | 3.510 |
| 240 | 14.950 | 8.447 | 4.719 |
| 1440 | 44.649 | 25.229 | 14.094 |

| | |
|---|---|
| Wafer mass (mg) | 179.000 |
| Intrinsic Dissolution Rate | 0.040 |

Example 9

Characterization of Curcumin-L-Lysine Co-Crystal

Figure 36:
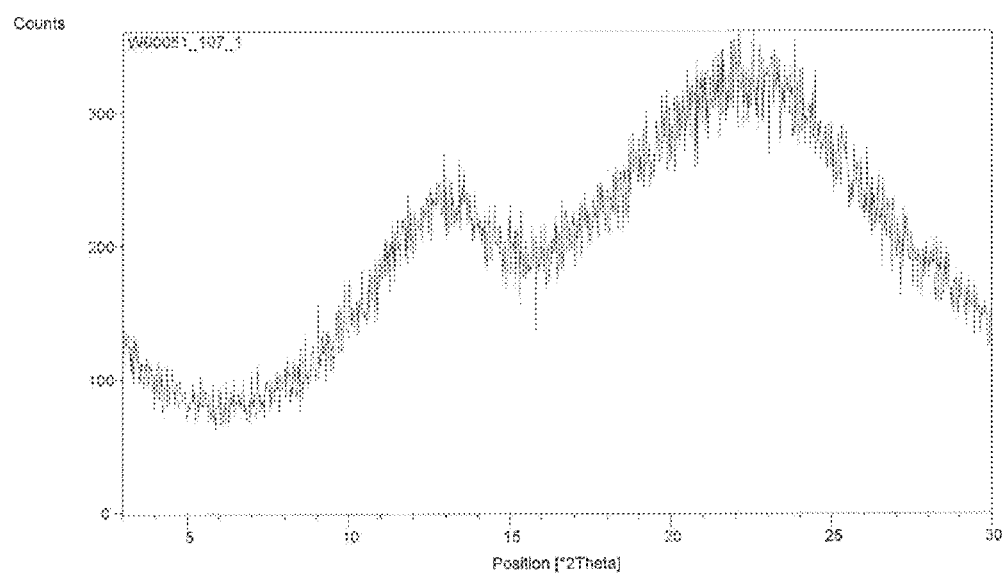
FIG. 36 depicts an X-ray powder diffraction (XRPD) pattern of curcumin co-crystal curcumin-L-lysine. Peak intensity is plotted as a function of degrees 2-theta.
Figure 42:
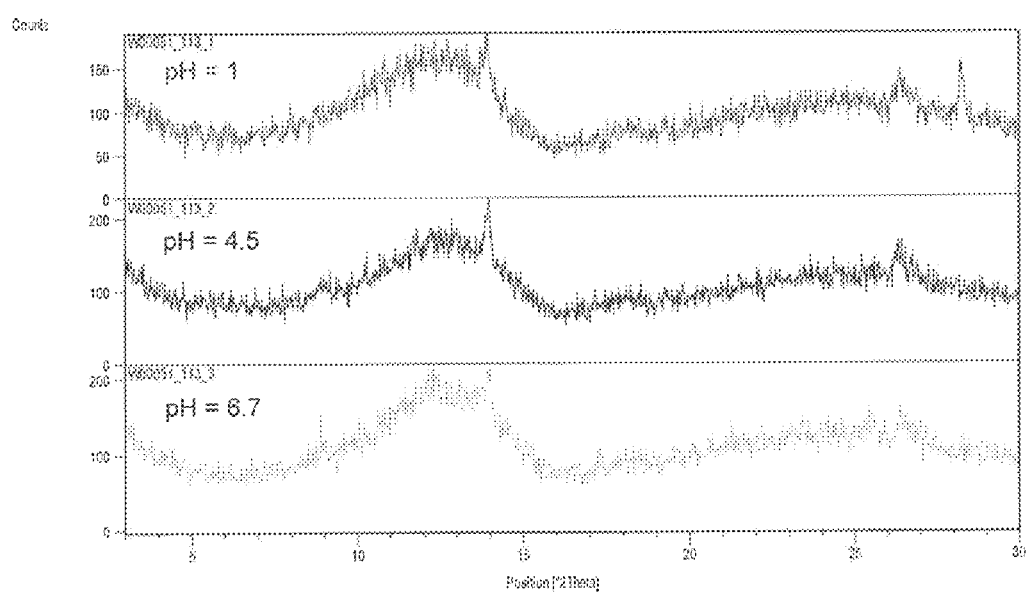
FIG. 42 depicts an X-ray powder diffraction (XRPD) pattern of curcumin co-crystal curcumin-L-lysine of thermodynamic solubility studies.

Curcumin-L-lysine remained amorphous during storage tests, slurring in water and DVS analysis. The material remained predominantly amorphous during thermodynamic solubility studies, although 2-3 small peaks could be seen by XRPD analysis (FIG. 36). The thermodynamic solubility of curcumin-L-lysine is also very low (FIG. 42). A dissolution rate of curcumin-L-lysine is 0.029.

Figure 35:
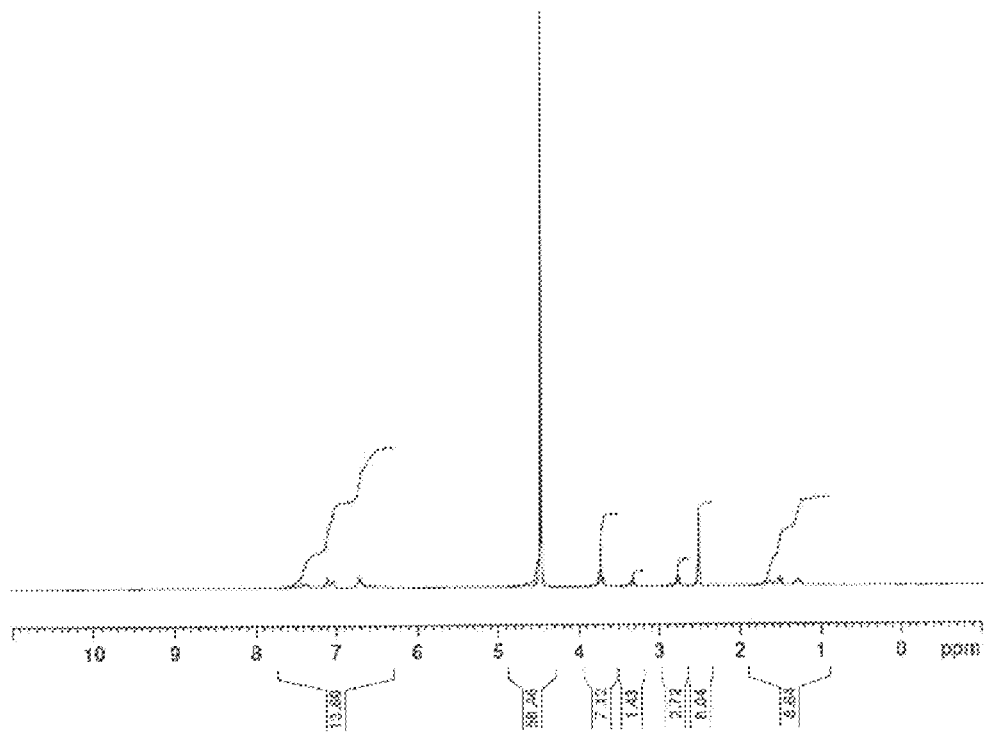
FIG. 35 depicts NMR $^1$H spectrum of curcumin co-crystal curcumin-L-lysine. The spectrum integrates to a 1:1 stoichiometry.
Figure 37:
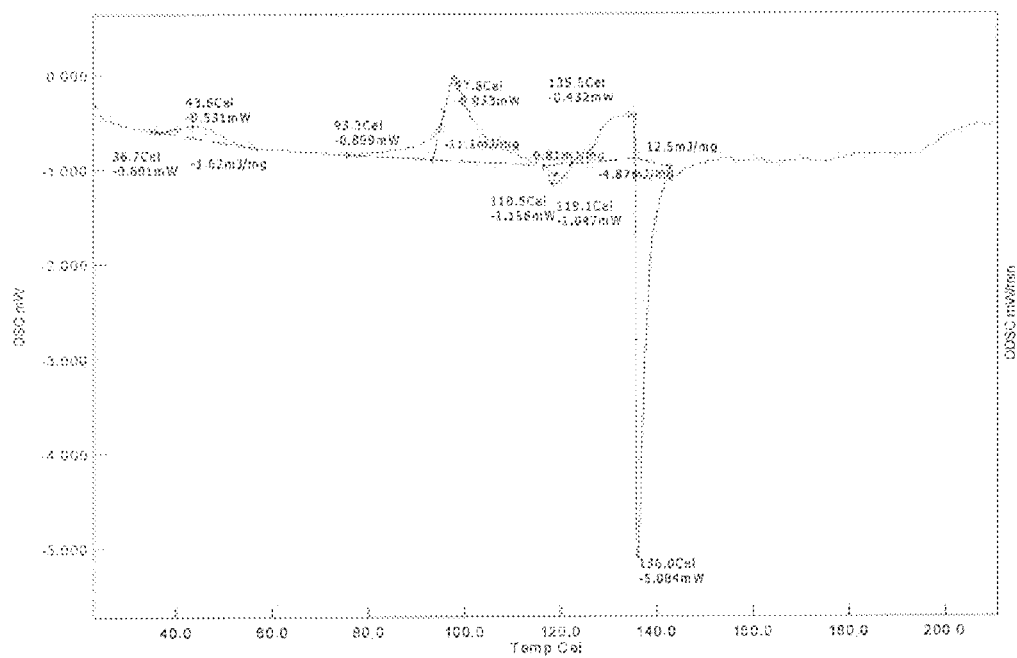
FIG. 37 depicts a differential scanning calorimetry (DSC) trace of curcumin co-crystal curcumin-L-lysine.
Figure 38:
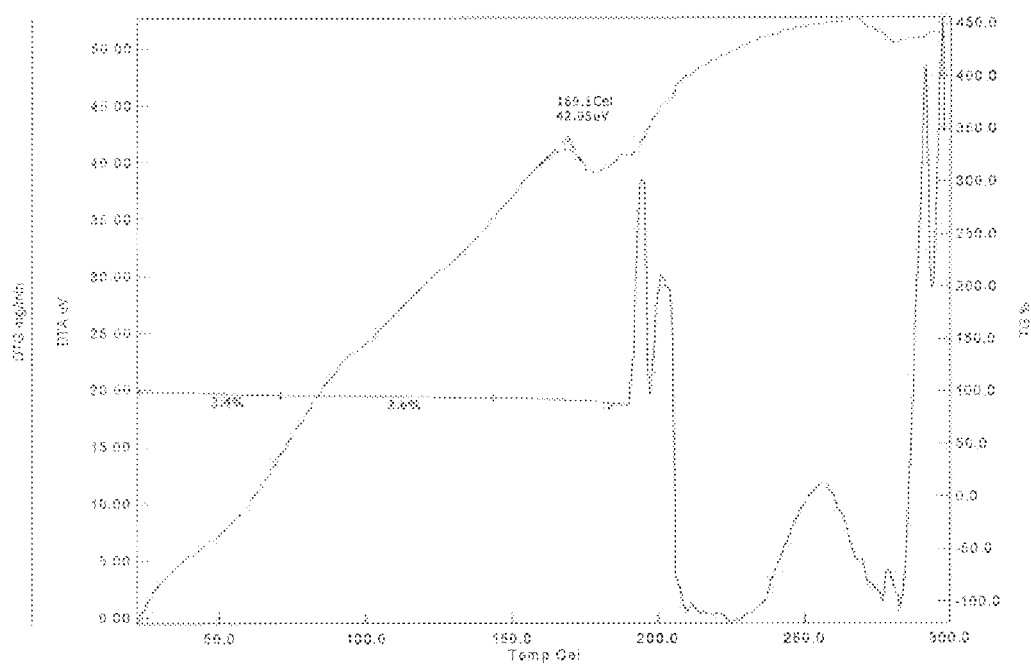
FIG. 38 depicts a thermogravimetric analysis (TGA) trace of curcumin co-crystal curcumin-L-lysine.

DSC shows a small, broad exotherm at onset 36.7° C. (peak 43.6° C.); second exotherm is seen at onset 93.7° C. (peak 97.8° C.); an endotherm is seen at onset 135.5° C. (peak 136.0° C.) (FIG. 37). The amorphous character of the material is evident in the DSC trace (FIG. 37). TGA/DTA shows a 3.4% weight loss from the outset followed by a second loss of 2.6%. This is likely due to unbound moisture (FIG. 38). The material likely starts to degrade above 169.1° C. The XRPD indicates that the material is amorphous. $^1$H NMR does not show signs of degradation (FIG. 35). The protons of the L-lysine can be accounted for in the spectrum. The spectrum almost integrates to a 1:1 stoichiometry.

Figure 39:
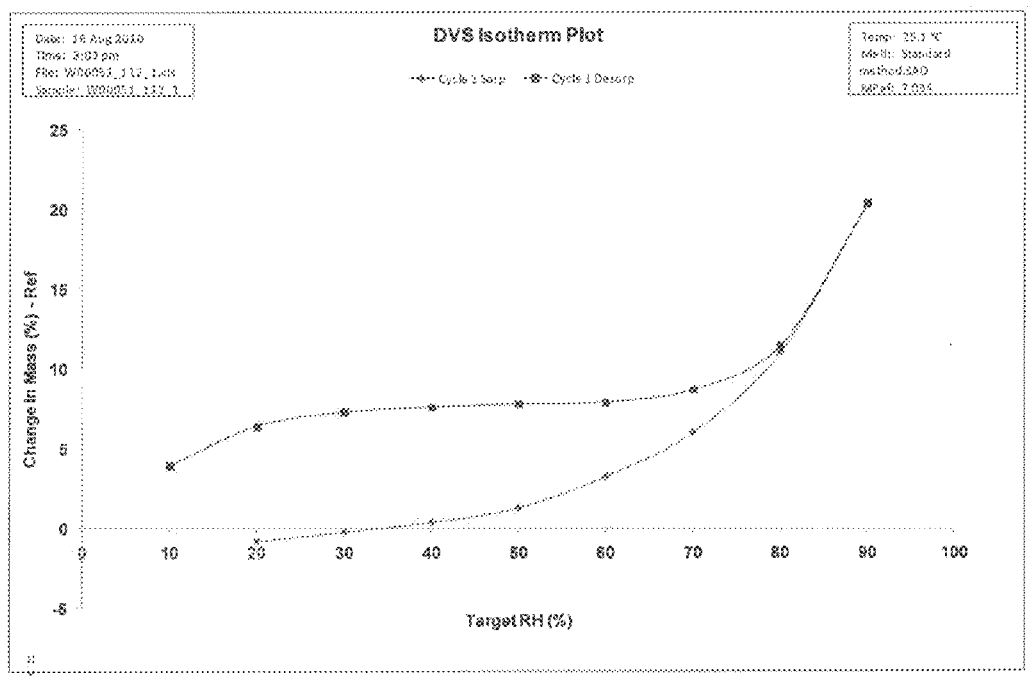
FIG. 39 depicts a dynamic vapor sorption (DVS) trace of curcumin co-crystal curcumin-L-lysine.
Figure 40:
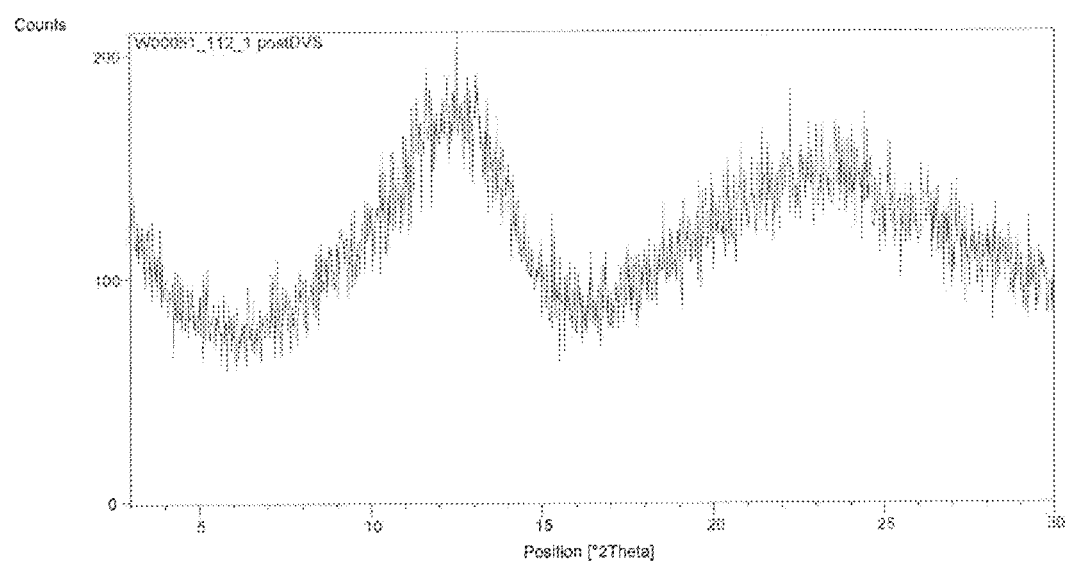
FIG. 40 depicts an X-ray powder diffraction (XRPD) pattern of curcumin co-crystal curcumin-L-lysine post the dynamic vapor sorption (DVS) analysis. Peak intensity is plotted as a function of degrees 2-theta.
Figure 41A:
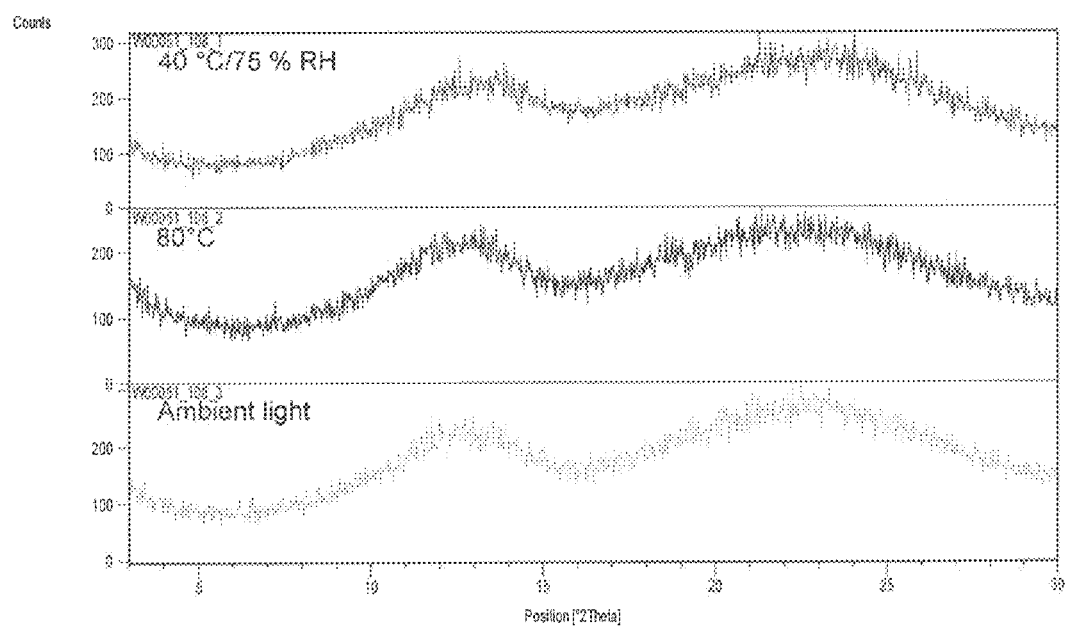
FIG. 41 depicts an X-ray powder diffraction (XRPD) pattern of curcumin co-crystal curcumin-L-lysine of (A) stability tests under 40° C./75% RH; 80° C.; and ambient light; of (B) slurrying in water. Peak intensity is plotted as a function of degrees 2-theta.
Figure 41B:
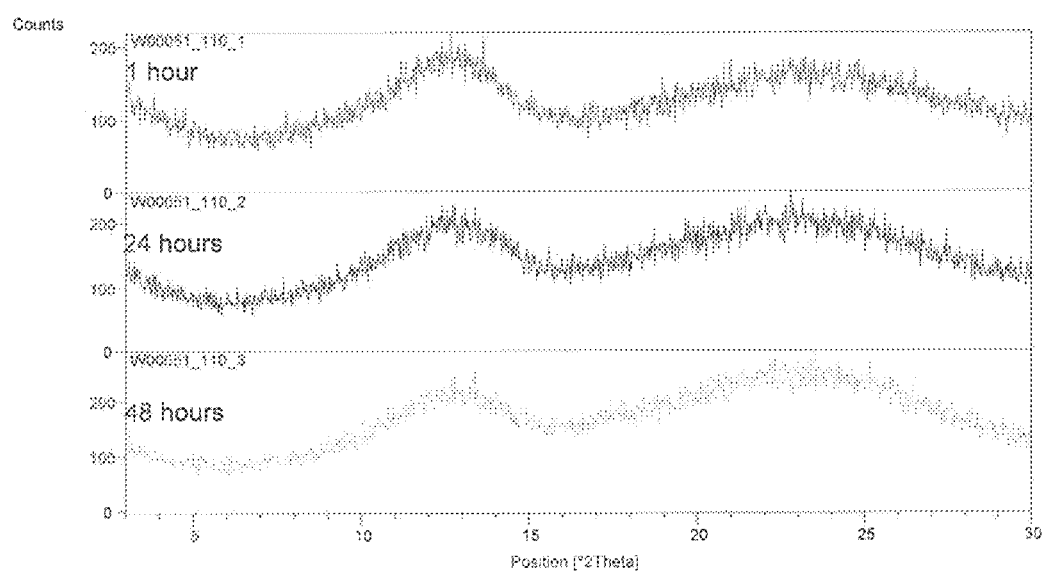

DVS analysis indicates a 6.81% water uptake between 20-70% RH. A 21.16% water uptake is shown between 20-90% RH (FIG. 39). The sample remains amorphous after post-DVS XRPD analysis (FIG. 40). Analysis after 1 week storage tests showed that the material remained amorphous. Slurrying the material in water resulted in the material remaining amorphous (FIG. 41 B). pH was monitored and results are as follows: after 1 hour, pH=9.53; after 48 hours, pH=9.41. After the thermodynamic solubility studies, XRPD analysis showed that the material was still predominantly amorphous however two or three small peaks could be seen in the diffractogram (FIG. 42). These peaks do not appear to correspond with curcumin or L-lysine. The thermodynamic solubility studies of the curcumin-L-lysine co-crystal showed very poor solubility in the various pH media (FIG. 42). The solubility appeared to increase slightly when using 1% solutol. The intrinsic dissolution rate of 0.029 is similar to that of the 2-aminobenzimidazole co-crystal (0.023) (Table 3). XRPD analysis carried out on the remainder of the dissolution wafer after 24 hours, indicated that it corresponded with the input curcumin material. The co-crystal therefore dissociated in the dissolution medium. This was also seen by a visible color change from dark purple at the outset, to a yellow/orange color corresponding with the color of curcumin. DSC analysis also showed an endotherm approximately corresponding with curcumin.

TABLE 3

L-lysine co-crystal dissolution data

| Timepoint (min) | Concentration (ug/ml) | Dissolution rate (mg/min/cm2) |
|---|---|---|
| 1 | 0.098 | 0.055 |
| 5 | 0.372 | 0.210 |
| 10 | 0.450 | 0.254 |
| 15 | 0.491 | 0.277 |
| 30 | 0.608 | 0.344 |
| 60 | 1.017 | 0.575 |
| 120 | 1.966 | 1.111 |
| 240 | 3.525 | 1.992 |
| 1440 | 47.788 | 27.003 |

| | |
|---|---|
| Intrinsic Dissolution Rate | 0.029 |

Note:
For cells with shaded backgrounds, the peak areas were below the limit of quantification.

Example 10

Cytotoxicity and Dose Response Analyses of Curcumin Crystal Forms

Figure 43:
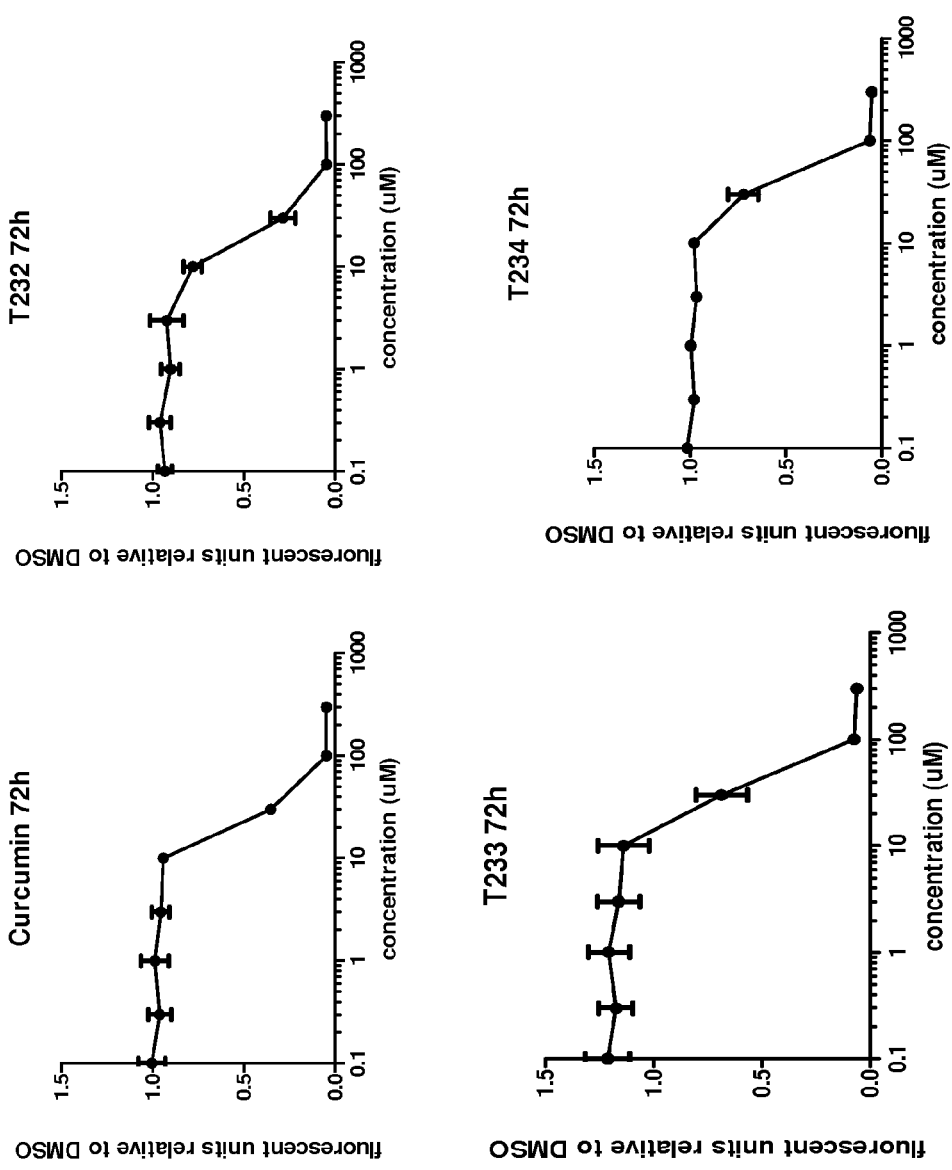
FIG. 43 depicts the cytotoxicity assay by Cell Titer Blue™. The cell viability via fluorescent units relative to DMSO was measured and plotted after a set of cell samples were treated for 72-hour with Curcumin, curcumin-2-aminobenzimidazole co-crystal (T232), curcumin-L-lysine co-crystal (T233) and Form III curcumin polymorph (T234), respectively, at a series of concentrations ranging from about 0.1 to about 300 μM. The $IC_{50}$ values in the logarithms form were comparison among the different solid forms of curcumin to evaluate drug potency. It showed that Log IC50 value was 29.7.2 for curcumin, 29.5 for curcumin-2-aminobenzimidazole co-crystal, 30.3 for curcumin-L-lysine co-crystal, and 49.9 for Form III curcumin polymorph.
Figure 45:
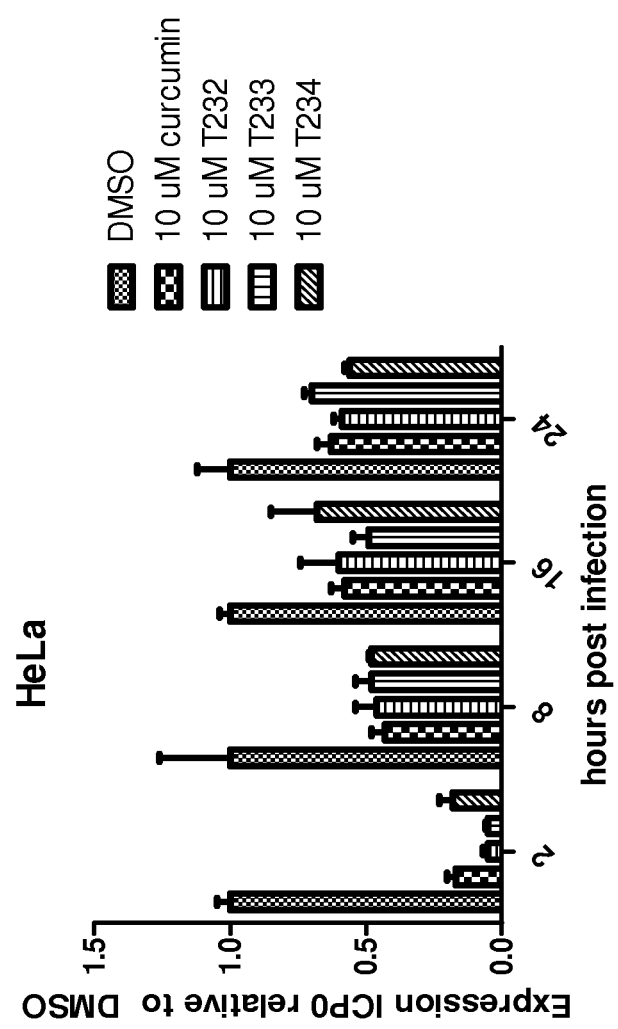
FIG. 45 depicted the diminished inhibition effect of different forms of curcumin crystal on HSV-1 viral immediate-early gene expression at late times. It showed that ICP0 gene expression was effectively inhibited by all four forms of curcumin crystal after 2 hours of treatment. However at 16 hour after treatment, the strength of the inhibition decreased, and after 24 hours of treatment, the inhibition by all four forms of curcumin crystal diminished dramatically in comparison to the inhibition effect at 2-hour point.

The cytotoxicity analysis of the curcumin crystal forms, including a curcumin and 2-aminobenzimidazole co-crystal (T232), curcumin and L-lysine co-crystal (T233) and a polymorph crystal form of curcumin, referred to as Form III above (T234) was carried out using the CellTiter-Blue™ (Promega) cell viability assay (FIG. 43). CellTiter-Blue™ Cell Viability Assay measures in vitro cell viability. The assay is based on the ability of living cells to convert a redox dye (resazurin) into a fluorescent end product (resorufin). Viable cells retain the ability to reduce resazurin into resorufin. Nonviable cells rapidly lose metabolic capacity, and thus, do not generate a fluorescent signal. The fluorescent signal from the CellTiter-Blue™ Reagent is directly proportional to the number of viable cells. In FIG. 43, cell viability via fluorescent units relative to DMSO was measured and plotted after a set of cell samples were treated for 72-hour treatment, the strength of the inhibition decreased, and after 16 hours of treatment, the inhibition by all 4 forms of curcumin crystal diminished dramatically in comparison to the inhibition effect at the 2-hour point (FIG. 45, Table 4).

TABLE 4

ICP0 gene expression under the effects of T compounds and curcumin

| | DMSO | | Curcumin | | T232 | | T233 | | T234 | |
|---|---|---|---|---|---|---|---|---|---|---|
| hpi | mean | sd | mean | sd | mean | sd | mean | sd | mean | sd |
| 2 | (1.0) | 0.05 | 0.17 | 0.03 | 0.05 | 0.02 | 0.05 | 0.01 | 0.18 | 0.05 |
| 8 | (1.0) | 0.26 | 0.43 | 0.05 | 0.46 | 0.08 | 0.48 | 0.06 | 0.48 | 0.01 |
| 16 | (1.0) | 0.04 | 0.58 | 0.05 | 0.6 | 0.14 | 0.49 | 0.06 | 0.68 | 0.17 |
| 24 | (1.0) | 0.12 | 0.63 | 0.05 | 0.59 | 0.03 | 0.7 | 0.03 | 0.56 | 0.02 | with curcumin, curcumin-2-aminobenzimidazole co-crystal, curcumin-L-lysine co-crystal and Form III curcumin polymorph, respectively, at a series of concentrations ranging from about 0.1 to about 300 µM. Curcumin, with known toxicity profile, was used as a positive control for $IC_{50}$ value comparison among the different solid forms of curcumin to evaluate drug potency. In some embodiments, the $IC_{50}$ value is less than 100 µM in order for the compound to be considered further for potential use for treatment. Log $IC_{50}$, the logarithm of an $IC_{50}$ value, may be used to achieve more linear data. FIG. 43 shows that $IC_{50}$ value in log units was 29.7 for curcumin, 29.5 for curcumin-2-aminobenzimidazole co-crystal, 30.3 for curcumin-L-lysine co-crystal, and 49.9 for Form III curcumin polymorph These results demonstrate that the new compounds have cytotoxicity profiles comparable to that of curcumin, and are not likely to be more hazardous in use than is curcumin.

Figure 44:
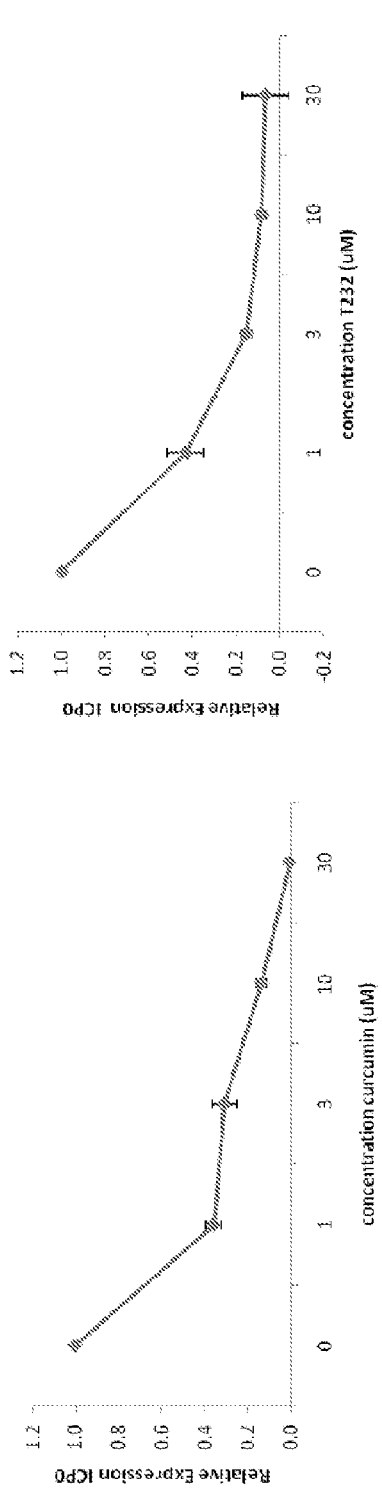
FIG. 44 depicted the dose response curves of HSV-1 ICP0 expression under the treatment of curcumin and other forms of curcumin crystals. It showed that the inhibition of ICP0 by the tested chemicals (T232, T233, T234) was dosage dependant, that the inhibition of ICP0 expression was about 60% at 1 μM with, and that the complete inhibition was achieved at 30 μM except for T232.
Figure 44:
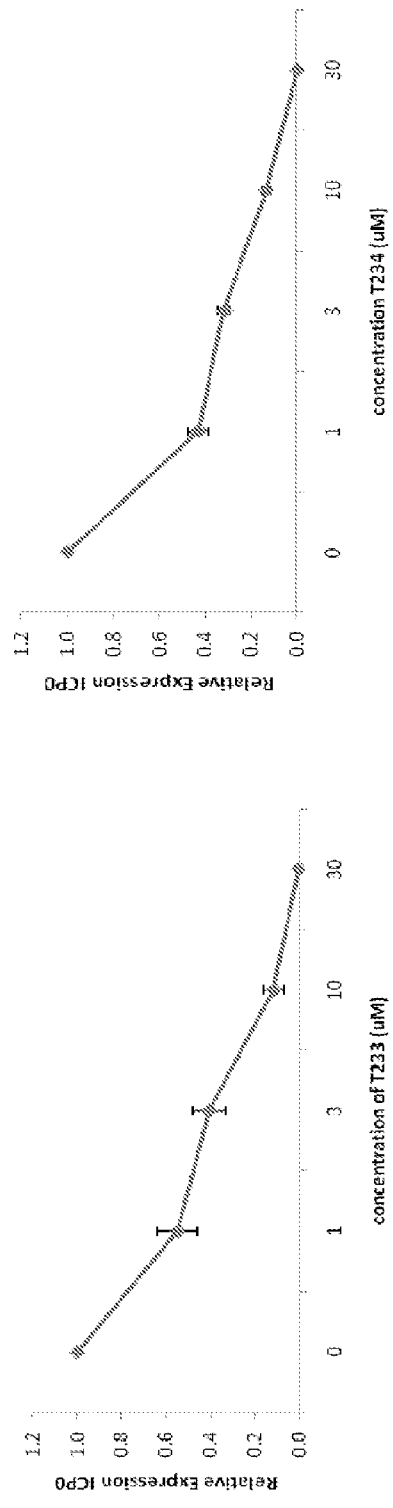

ICP0 is an immediate-early (IE) regulatory protein, and is a potent activator of herpes simplex virus type 1 gene expression in lytic infection and in the establishment and reactivation of latency in vivo. Curcumin is known to have antiviral effects. For example, it inhibits the expression of ICP0 in a dose-dependent manner. Dose response analyses were carried out to evaluate the potency of curcumin-2-aminobenzimidazole co-crystal, curcumin-L-lysine co-crystal and for Form III curcumin polymorph to inhibit the ICP0 expression in HSV-1 virus at concentrations of 0, 1 µM, 3 µM, 10 µM and 30 µM, with curcumin as the positive control (FIG. 44). FIG. 44 shows that the inhibition of ICP0 by the tested chemicals (T232, T233, T234) was dosage dependent, that the inhibition of ICP0 expression was about 60% at 1 µM, and that complete inhibition was achieved at 30 µM, except for T232.

10 µM T232, 10 µM T233 and 10 µM T234 were selected for further demonstration of various curcumin crystals' effects on HSV-1 viral immediate-early gene ICP0 expression through time course of infection of Hela cells, using 10 µM curcumin as control (FIG. 45). Expression levels of the viral immediate-early gene ICP0 were assayed by reverse transcription followed by quantitative polymerase chain reaction. Values indicate the expression of ICP0 relative to the cellular 18S rRNA, as calculated by the $2^{\wedge}$-$\Delta$Ct method that is standard for quantitative PCR (where Ct refers to cycles required to reach threshold, and delta refers to difference in Ct value for ICP0 and 18S rRNA in any given sample). These values were then normalized to the DMSO vehicle control. FIG. 45 shows that ICP0 gene expression was effectively inhibited by all 4 forms of curcumin crystal after 2 hours of treatment. However, after 8 hours of

What is claimed is:

1. A co-crystal form of curcumin, wherein the co-crystal form is curcumin-2-aminobenzimidazole.

2. The co-crystal form of claim 1, wherein curcumin-2-aminobenzimidazole exhibits an X-ray powder diffraction pattern having characteristic peaks expressed in degrees-2-theta at about 6.2, about 9.0, about 12.3, about 14.5, about 17.3, about 18.0, about 19.0, about 20.0, about 21.2, about 24.5, about 25.05, and about 27.1, and further exhibits an endothermic transition with an onset of about 118.1° C. as measured by differential scanning calorimetry.

3. A co-crystal form of curcumin, wherein the co-crystal form is curcumin-L-lysine.

4. The co-crystal form of claim 3, wherein curcumin-L-lysine is an amorphous form of curcumin co-crystal; and exhibits a first exotherm at onset 36.7° C. with peak 43.6° C., a second exotherm at onset 93.7° C. with peak 97.8° C., and an endotherm at onset 135.5° C. with peak 136.0° C.

5. A polymorph form of curcumin, wherein the polymorph form is Form III.

6. The polymorph form of claim 5, wherein Form III exhibits X-ray powder diffraction pattern having characteristic peaks expressed in degrees 2-theta at about 9.56, about 14.51, about 17.90, and about 26.86, and exhibits an endothermic transition with an onset of about 162.6° C. as measured by differential scanning calorimetry.

7. A pharmaceutical composition, the composition comprising at least one compound selected from the group consisting of curcumin polymorph Form III, curcumin-2-aminobenzimidazole, and curcumin-L-lysine and at least one pharmaceutically acceptable excipient.

8. The pharmaceutical composition of claim 7, wherein the curcumin polymorph Form III exhibits X-ray powder diffraction pattern having characteristic peaks expressed in degrees 2-theta at about 9.56, about 14.51, about 17.90, and about 26.86 and an endothermic transition with an onset of about 162.6° C. as measured by differential scanning calorimetry.

9. The pharmaceutical composition of claim 7, wherein the curcumin-2-aminobenzimidazole co-crystal exhibits an X-ray powder diffraction pattern having characteristic peaks expressed in degrees 2-theta at about 6.2, about 9.0, about 12.3, about 14.5, about 17.3, about 18.0, about 19.0, about 20.0, about 21.2, about 24.5, about 25.05, and about 27.1 and an endothermic transition with an onset of about 118.1° C. as measured by differential scanning calorimetry.

10. The pharmaceutical composition of claim 7, wherein the curcumin-L-lysine exhibits a first exotherm at onset 36.7° C. with peak 43.6° C.; a second exotherm at onset 93.7° C. with peak 97.8° C.; and an endotherm at onset 135.5° C. with peak 136.0° C.

11. A method of inhibiting cancer cell growth, in cancers of the breast, uterus, cervix, prostate or GI tract wherein the method comprises administering an effective dosage amount of a composition comprising at least one compound selected from the group consisting of curcumin polymorph Form III, curcumin-2-aminobenzimidazole, and curcumin-L-lysine to a subject having said cancer.

12. The method of claim 11, wherein the curcumin polymorph Form III exhibits an X-ray powder diffraction pattern having characteristic peaks expressed in degrees 2-theta at about 9.56, about 14.51, about 17.90, and about 26.86 and an endothermic transition with an onset of about 162.6° C. as measured by differential scanning calorimetry.

13. The method of claim 11, wherein the curcumin-2-aminobenzimidazole exhibits an X-ray powder diffraction pattern having characteristic peaks expressed in degrees 2-theta at about 6.2, about 9.0, about 12.3, about 14.5, about 17.3, about 18.0, about 19.0, about 20.0, about 21.2, about 24.5, about 25.05, and about 27.1 and an endothermic transition with an onset of about 118.1 ° C. as measured by differential scanning calorimetry.

14. The method of claim 11, wherein the curcumin-L-lysine exhibits a first exotherm at onset 36.7° C. with peak 43.6° C.; a second exotherm at onset 93.7° C., with peak 97.8° C.; and an endotherm at onset 135.5° C. with peak 136.0° C.

15. A method of inhibiting the growth of HSV-1, wherein the method comprises administering an effective dosage amount of a composition comprising at least one compound selected from the group consisting of curcumin polymorph Form III, curcumin-2-aminobenzimidazole, and curcumin-L-lysine to a subject having HSV-1.

16. The method of claim 15, wherein the curcumin polymorph Form III exhibits an X-ray powder diffraction pattern having characteristic peaks expressed in degrees 2-theta at about 9.56, about 14.51, about 17.90, and about 26.86 and an endothermic transition with an onset of about 162.6° C. as measured by differential scanning calorimetry.

17. The method of claim 15, wherein the curcumin-2-aminobenzimidazole exhibits an X-ray powder diffraction pattern having characteristic peaks expressed in degrees 2-theta at about 6.2, about 9.0, about 12.3, about 14.5, about 17.3, about 18.0, about 19.0, about 20.0, about 21.2, about 24.5, about 25.05, and about 27.1 and an endothermic transition with an onset of about 118.1° C. as measured by differential scanning calorimetry.

18. The method of claim 15, wherein the curcumin-L-lysine exhibits a first exotherm at onset 36.7° C. with peak 43.6° C.; a second exotherm at onset 93.7° C., with peak 97.8° C.; and an endotherm at onset 135.5° C. with peak 136.0° C.

* * * * *